US006994847B2

(12) United States Patent
Wolfe et al.

(10) Patent No.: US 6,994,847 B2
(45) Date of Patent: Feb. 7, 2006

(54) STABILIZED INTERFERON COMPOSITIONS

(75) Inventors: Sidney N. Wolfe, Lafayette, CA (US); Maninder S. Hora, Danville, CA (US)

(73) Assignee: Chiron Corporation, Emeryville, CA (US)

( * ) Notice: Subject to any disclaimer, the term of this patent is extended or adjusted under 35 U.S.C. 154(b) by 318 days.

(21) Appl. No.: 10/010,448

(22) Filed: Nov. 7, 2001

(65) Prior Publication Data

US 2002/0114782 A1 Aug. 22, 2002

Related U.S. Application Data

(60) Provisional application No. 60/252,224, filed on Nov. 21, 2000, provisional application No. 60/246,456, filed on Nov. 7, 2000.

(51) Int. Cl.
*A61K 38/21* (2006.01)
*A61K 39/00* (2006.01)
*C12N 9/96* (2006.01)
*C07K 14/00* (2006.01)

(52) U.S. Cl. ............... 424/85.6; 424/198.1; 435/188; 530/412; 530/422; 530/351

(58) Field of Classification Search ............... 424/85.6, 424/198.1; 530/412, 422, 351; 435/188
See application file for complete search history.

(56) References Cited

U.S. PATENT DOCUMENTS

| 4,439,181 | A | | 3/1984 | Blackshear et al. |
|---|---|---|---|---|
| 4,462,940 | A | | 7/1984 | Hanisch et al. |
| 4,465,622 | A | | 8/1984 | Nobuhara et al. |
| 4,605,555 | A | | 8/1986 | Sato et al. |
| 4,605,556 | A | | 8/1986 | Sato et al. |
| 4,647,454 | A | | 3/1987 | Cymbalista |
| 4,675,184 | A | | 6/1987 | Hasegawa et al. |
| 4,808,705 | A | * | 2/1989 | Ferris ..................... 424/183.1 |
| 4,816,440 | A | | 3/1989 | Thomson |
| 4,992,271 | A | | 2/1991 | Hanisch et al. |
| 5,004,605 | A | | 4/1991 | Hershenson et al. |
| 5,104,651 | A | | 4/1992 | Boone et al. |
| 5,151,265 | A | | 9/1992 | Hwang-Felgner et al. |
| 5,183,746 | A | | 2/1993 | Shaked et al. |
| 5,573,777 | A | | 11/1996 | Serpelloni et al. |
| 5,609,868 | A | | 3/1997 | Lowther et al. |
| 5,643,566 | A | | 7/1997 | Hanisch et al. |
| 5,702,699 | A | | 12/1997 | Hanisch et al. |
| 5,762,923 | A | | 6/1998 | Gross et al. |
| 5,763,409 | A | | 6/1998 | Bayol et al. |

FOREIGN PATENT DOCUMENTS

| EP | 0 080 879 B1 | 10/1986 |
|---|---|---|
| EP | 0 217 645 B1 | 4/1987 |
| EP | 0 270 799 B1 | 6/1988 |
| EP | 0 164 397 B1 | 7/1990 |
| EP | 0 410 207 A2 | 1/1991 |
| EP | 0 410 207 B1 | 1/1991 |
| EP | 0 133 767 B1 | 4/1991 |
| EP | 0 477 386 B1 | 1/1992 |
| EP | 0 215 658 B1 | 6/1994 |
| EP | 0 736 303 B1 | 10/1996 |
| EP | 0 759 775 B1 | 3/1997 |
| EP | 0 875 253 A2 | 11/1998 |
| WO | WO 90/06762 | 6/1990 |
| WO | WO 91/16038 | 10/1991 |
| WO | WO 95/31213 | 11/1995 |
| WO | WO 95/31479 | 11/1995 |

OTHER PUBLICATIONS

Dubost, D.C. et al., "Characterization of a Solid State Reaction Product from a Lyophilized Formulation of a Cyclic Heptapeptide. A Novel Example of an Excipient-Induced Oxidation," *Pharmaceutical Research*, Dec. 1996, pp. 1811-1814, vol. 13, No. 12.

Herberman et al., "Augmentation by Interferon of Human Natural and Antibody-Dependent Cell-Mediated Cytotoxicity" *Nature* 277:221-223, Jan. 1979.

Williams et al., "Natural Ocurrence of 2-5A in Interferon-Treated EMC Virus-Infected L Cells" *Nature* 282:582-586, 1979.

Anderson et al., "Specific Binding of $^{125}$I-Human Inerferon-γ to High Affinity Receptors of Human Fibroblasts" *J. Biological Chemistry* 257 (19) :11301-11304, 1982.

Fellous et al., "Interferon-Dependent Inductionof mRNA for the Major Histocampatibility Antigens in Human Fibroblasts and Lymphoblastoid Cells" *Proc. Natl. Acad. Sci. 79*: 3082- 3086, May, 1982.

Czarniecki et al., "Syneristic Antiviral and Antiproliferative Activities of *Escherichia coli*-Derived Human Alpha, Beta, and Gamma Interferons" *J. Virology* 49(2) :490=496, Feb. 1984.

Mark et al., "Site-Specific Mutagenesis of the Human Fibroblast Interferon Gene" *Proc. Natl. Acad. Sci. USA 81* :5662-5666, Sep., 1984.

* cited by examiner

*Primary Examiner*—Janet Andres
(74) *Attorney, Agent, or Firm*—Leslie Henry; Gerald Suh; Alisa A. Harbin

(57) ABSTRACT

Stabilized pharmaceutical formulations comprising IFN-β and highly purified mannitol are provided. The highly purified mannitol stabilizes the compositions by reducing the formation of IFN-β adducts in comparison with IFN-β formulated with mannitol that has not been highly purified. Methods for increasing the stability of IFN-β or a variant thereof in a liquid or lyophilized composition and for increasing storage stability of such a composition are also provided.

77 Claims, 20 Drawing Sheets

STABILITY EVALUATION DATA
Interferon-β-1b: Dextrose Formulation

| Product | Storage Temperature (upright, protected from light) | Months | Potency (Specific activity, IU/mg) | Glucosylated IFN-β-1b concentration (mg/ml) | Total IFNβ-1b concentration (mg/ml) |
|---|---|---|---|---|---|
| IFN-β 1b 0.25 mg/ml 1.25 % dextrose 1.25 % HSA Lot: MBAPM023 7200-607 | +8°C | 0 | $2.13 \times 10^7$ | <0.02 | 0.22 |
| | +8°C | 1 | $2.50 \times 10^7$ | <0.02 | 0.23 |
| | +8°C | 2 | $2.71 \times 10^7$ | <0.02 | 0.23 |
| | +50°C | 2.2 | $3.52 \times 10^7$ | <0.02 | 0.23 |
| | +50°C | 2.5 | $4.68 \times 10^7$ | Too degraded | Too degraded |
| | +50°C | 2.7 | $4.60 \times 10^7$ | Too degraded | Too degraded |
| | +50°C | 3 | $5.61 \times 10^7$ | Too degraded | Too degraded |
| | +8°C | 3 | $2.41 \times 10^7$ | <0.02 | 0.23 |
| IFN-β 1b 0.25 mg/ml 1.25 % dextrose 1.25 % HSA Lot: MBAPM027 7200-600 | +25°C | 0 | $2.12 \times 10^7$ | <0.02 | 0.22 |
| | +25°C | 1 | $2.05 \times 10^7$ | <0.02 | 0.21 |
| | +25°C | 2 | $3.24 \times 10^7$ | <0.02 | 0.22 |
| | +50°C | 2.2 | $3.88 \times 10^7$ | <0.02 | 0.21 |
| | +50°C | 2.5 | $4.64 \times 10^7$ | Too degraded | Too degraded |
| | +50°C | 2.7 | $5.08 \times 10^7$ | Too degraded | Too degraded |
| | +50°C | 3 | $5.91 \times 10^7$ | Too degraded | Too degraded |
| | +25°C | 3 | $2.51 \times 10^7$ | <0.02 | 0.23 |
| IFN-β 1b 0.25 mg/ml 1.25 % dextrose 1.25 % HSA Lot: MBAPM027 7200-600 | +37°C | 0 | $2.12 \times 10^7$ | <0.02 | 0.22 |
| | +37°C | 1 | $2.85 \times 10^7$ | <0.02 | 0.18 |
| | +37°C | 2 | $3.88 \times 10^7$ | <0.02 | 0.23 |
| | +50°C | 2.2 | $4.28 \times 10^7$ | Too degraded | Too degraded |
| | +50°C | 2.5 | $4.88 \times 10^7$ | Too degraded | Too degraded |
| | +50°C | 2.7 | $4.72 \times 10^7$ | Too degraded | Too degraded |
| | +50°C | 3 | $5.44 \times 10^7$ | Too degraded | Too degraded |
| | +37°C | 3 | $4.08 \times 10^7$ | Too degraded | Too degraded |

FIGURE 12

STABILITY EVALUATION DATA
Interferon-β-1b: Highly Purified Mannitol Formulation

| Product | Storage Temperature (upright, protected from light) | Months | Potency (Specific activity, IU/mg) | Glucosylated IFN-β-1b concentration (mg/ml) | Total IFNβ-1b concentration (mg/ml) |
|---|---|---|---|---|---|
| IFN-β 1b 0.25 mg/ml 1.25 % highly purified mannitol 1.25 % HSA | +8°C | 0 | $1.40 \times 10^7$ | <0.02 | 0.22 |
| | +8°C | 1 | $1.52 \times 10^7$ | <0.02 | 0.21 |
| | +8°C | 2 | $1.69 \times 10^7$ | <0.02 | 0.22 |
| | +50°C | 2.2 | $1.68 \times 10^7$ | <0.02 | 0.22 |
| | +50°C | 2.5 | $1.68 \times 10^7$ | <0.02 | 0.21 |
| | +50°C | 2.7 | $1.54 \times 10^7$ | <0.02 | 0.21 |
| | +50°C | 3 | $1.53 \times 10^7$ | <0.02 | 0.22 |
| | +8°C | 3 | $1.62 \times 10^7$ | <0.02 | 0.23 |
| IFN-β 1b 0.25 mg/ml 1.25 % highly purified mannitol 1.25 % HSA | +25°C | 0 | $1.40 \times 10^7$ | <0.02 | 0.22 |
| | +25°C | 1 | $1.58 \times 10^7$ | <0.02 | 0.21 |
| | +25°C | 2 | $1.88 \times 10^7$ | <0.02 | 0.22 |
| | +50°C | 2.2 | $1.84 \times 10^7$ | <0.02 | 0.22 |
| | +50°C | 2.5 | $1.67 \times 10^7$ | <0.02 | 0.20 |
| | +50°C | 2.7 | $1.61 \times 10^7$ | <0.02 | 0.21 |
| | +50°C | 3 | $1.53 \times 10^7$ | <0.02 | 0.22 |
| | +25°C | 3 | $1.59 \times 10^7$ | <0.02 | 0.23 |
| IFN-β 1b 0.25 mg/ml 1.25 % highly purified mannitol 1.25 % HSA | +37°C | 0 | $1.40 \times 10^7$ | <0.02 | 0.22 |
| | +37°C | 1 | $1.50 \times 10^7$ | <0.02 | 0.21 |
| | +37°C | 2 | $1.80 \times 10^7$ | <0.02 | 0.21 |
| | +50°C | 2.2 | $1.86 \times 10^7$ | <0.02 | 0.21 |
| | +50°C | 2.5 | $1.84 \times 10^7$ | <0.02 | 0.20 |
| | +50°C | 2.7 | $1.73 \times 10^7$ | <0.02 | 0.20 |
| | +50°C | 3 | $1.41 \times 10^7$ | <0.02 | 0.20 |
| | +37°C | 3 | $1.53 \times 10^7$ | <0.02 | 0.22 |

FIGURE 13

STABILITY OF BETASERON/BETAFERON FINAL CONTAINER PRODUCT
RESULTS FOR LOT MBDPN005 (MANNITOL FORMULATION)

| Storage Temp. (°C) | Months in Storage | Appearance Plug (cake) | Upon Reconstitution | Upon Recon. Clarity | Upon Recon. Color | Residual Moisture (% by weight) | pH Upon Reconstitution | Potency CPE Bioassay (IU/mg x10⁷) | Container Closure Integrity Dye Leak Test | Sterility |
|---|---|---|---|---|---|---|---|---|---|---|
| 4 | 0 | white | clear, slightly yellow | -- | -- | 0.3 | 7.4 | 2.3 | -- | Pass |
| 4 | 2 | -- | -- | -- | -- | 0.4 | -- | -- | -- | -- |
| 4 | 3 | white | clear, colorless | -- | -- | 0.5 | 7.3 | 2.8 | -- | -- |
| 4 | 4 | -- | -- | -- | -- | 0.4 | -- | -- | -- | -- |
| 4 | 5 | -- | -- | -- | -- | -- | -- | -- | -- | -- |
| 4 | 6 | white | clear, colorless | -- | -- | 0.4 | 7.3 | 3.4 | -- | -- |
| 4 | 9 | white | clear, colorless | -- | -- | 0.5 | 7.4 | 3.3 | -- | -- |
| 4 | 12 | white | clear, colorless | -- | -- | 0.5 | 7.5 | 3.2 | -- | -- |
| 4 | 18 | white | clear, slightly yellow | <II | colorless | 0.6 | 7.4 | 3.3 | -- | -- |
| 4 | 24 | white | clear, slightly yellow | <II | >BY₇ | 0.6 | 7.5 | 3.2 | Pass | Pass |
| 30 | 2 | -- | -- | -- | -- | 0.7 | -- | -- | -- | -- |
| 30 | 3 | white | clear, colorless | <II | <BY₄ | 0.6 | 7.3 | 3.3 | -- | -- |
| 30 | 4 | -- | -- | -- | -- | 0.6 | -- | -- | -- | -- |
| 30 | 5 | -- | -- | -- | -- | -- | -- | -- | -- | -- |
| 30 | 6 | white | clear, slightly yellow | <II | BY₆ | 0.7 | 7.4 | 3.1 | -- | -- |
| 30 | 9 | white | clear, colorless | <II | <BY₆ | 0.8 | 7.5 | 3.1 | -- | -- |
| 30 | 12 | white | clear, colorless | -- | -- | 0.8 | 7.5 | 3.6 | -- | -- |
| 30 | 18 | white | clear, slightly yellow | <II | colorless | 1.0 | 7.4 | 2.8 | -- | -- |
| 30 | 24 | white | clear, slightly yellow | <II | >BY₇ | 1.1 | 7.4 | 3.3 | Pass | Pass |
| European Specifications: | | White | Clear, colorless to light yellow | NMT Ref III | Colorless to slightly yellow NMTBY₃ | NMT 3% | 7.1-7.8 | 2.2 to 4.5 x 10⁷ | Pass | Pass |

FIGURE 14(A)

STABILITY OF BETASERON / BETAFERON FINAL CONTAINER PRODUCT
RESULTS FOR LOT MBDPN006 (MANNITOL FORMULATION)

| Storage Temp. (°C) | Months in Storage | RP-HPLC Analysis | |
|---|---|---|---|
| | | Interferon beta-1b (Peak B + Peak B1) (mg/ml) | Peak B1 (glucosylated) (mg/ml) |
| 4 | 0 | — | — |
| 4 | 2 | — | — |
| 4 | 3 | — | — |
| 4 | 4 | — | — |
| 4 | 5 | 0.24 | <0.02 |
| 4 | 6 | 0.25*** | <0.02*** |
| 4 | 9 | 0.23*** | <0.02*** |
| 4 | 12 | 0.23 | <0.02 |
| 4 | 18 | 0.25 | <0.02 |
| 4 | 24 | 0.25 | <0.02 |
| 30 | 2 | — | — |
| 30 | 3 | — | — |
| 30 | 4 | — | — |
| 30 | 5 | 0.23 | <0.02 |
| 30 | 6 | 0.25*** | <0.02*** |
| 30 | 9 | 0.23*** | <0.02*** |
| 30 | 12 | 0.23 | <0.02 |
| 30 | 18 | 0.24 | <0.02 |
| 30 | 24 | 0.25 | <0.02 |
| Expected Results | | 0.25±0.04 | NMT 0.02 |

*** SOP QG162 (AKA Q1052) was not followed: NLT one injection per test vial (two test vials per lot) was not performed.

FIGURE 14(B)

STABILITY OF BETASERON J BETAFERON FINAL CONTAINER PRODUCT
RESULTS FOR LOT MEDPN008 (MANNITOL FORMULATION)

| Storage Temp. (°C) | Months in Storage | Appearance Plug (cake) | Appearance Upon Reconstitution | Upon Recon. Clarity | Upon Recon. Color | Residual Moisture (% by weight) | pH Upon Reconstitution | Potency CPE Bioassay (IU/mg x10⁷) | Container Closure Integrity Dye Leak Test | Sterility |
|---|---|---|---|---|---|---|---|---|---|---|
| 4 | 0 | white | clear, colorless | - | - | 0.3 | 7.3 | 2.9 | - | Pass |
| 4 | 2 | - | - | - | - | 0.5 | - | - | - | - |
| 4 | 3 | white | clear, colorless | - | - | 0.5 | 7.4 | 2.7 | - | - |
| 4 | 4 | - | - | - | - | 0.5 | - | - | - | - |
| 4 | 5 | - | - | - | - | - | - | - | - | - |
| 4 | 6 | white | clear, colorless | - | - | 0.5 | 7.5 | 3.3 | - | - |
| 4 | 9 | white | clear, colorless | - | - | 0.6 | 7.6 | 3.4 | - | - |
| 4 | 12 | white | clear, colorless | - | - | 0.6 | 7.6 | 3.2 | - | - |
| 4 | 18 | white | clear, colorless | <III | colorless | 0.6 | 7.5 | 2.8 | - | - |
| 4 | 24 | white | clear, slightly yellow | <III | >BY₇ | 0.6 | 7.6 | 3.3 | Pass | Pass |
| 30 | 2 | - | - | - | - | 0.7 | - | - | - | - |
| 30 | 3 | white | clear, colorless | <III | - | 0.7 | 7.5 | 3.0 | - | - |
| 30 | 4 | - | - | - | - | 0.6 | - | - | - | - |
| 30 | 5 | - | - | - | - | - | - | - | - | - |
| 30 | 6 | white | clear, slightly yellow | <III | BY₆ | 0.7 | 7.5 | 3.4 | - | - |
| 30 | 9 | white | clear, colorless | II | <BY₆ | 1.0 | 7.6 | 3.4 | - | - |
| 30 | 12 | white | clear, colorless | - | - | 0.9 | 7.6 | 3.2 | - | - |
| 30 | 18 | white | clear, colorless | III | colorless | 1.0 | 7.6 | 2.9 | - | - |
| 30 | 24 | white | clear, slightly yellow | <III | >BY₇ | 1.1 | 7.6 | 3.2 | Pass | Pass |
| European Specifications | | White | Clear, colorless to light yellow | NMT RefIII | Colorless to slightly yellow BY₅ | NMT 3% | 7.1-7.8 | 2.2 to 4.5 x10⁷ | Pass | Pass |

FIGURE 15(A)

STABILITY OF BETASERON / BETAFERON FINAL CONTAINER PRODUCT
RESULTS FOR LOT MBDPN008 (MANNITOL FORMULATION)

| Storage Temp. (°C) | Months in Storage | RP-HPLC Analysis | |
|---|---|---|---|
| | | Interferon beta-1b (Peak B + Peak B1) [mg/ml] | Peak B1 (glucosylated) [mg/ml] |
| 4 | 0 | — | — |
| 4 | 2 | — | — |
| 4 | 3 | — | — |
| 4 | 4 | — | — |
| 4 | 5 | 0.23 | <0.02 |
| 4 | 6 | 0.24*** | <0.02*** |
| 4 | 9 | 0.23*** | <0.02*** |
| 4 | 12 | 0.23 | <0.02 |
| 4 | 18 | 0.24 | <0.02 |
| 4 | 24 | 0.25 | <0.02 |
| 30 | 2 | — | — |
| 30 | 3 | — | — |
| 30 | 4 | — | — |
| 30 | 5 | 0.23 | <0.02 |
| 30 | 6 | 0.24*** | <0.02*** |
| 30 | 9 | 0.22*** | <0.02*** |
| 30 | 12 | 0.22 | <0.02 |
| 30 | 18 | 0.23 | <0.02 |
| 30 | 24 | 0.23 | <0.02 |
| Expected Results: | | 0.25 ± 0.04 | NMT 0.02 |

*** SOP QG162 (AKA Q1052) was not followed: NLT one injection per test vial (two test vials per lot) was not performed
Note: A correction was made to the 18 month data point for RP-HPLC.

FIGURE 15(B)

STABILITY OF BETASERON / BETAFERON FINAL CONTAINER PRODUCT
RESULTS FOR LOT MBDEN009 (MANNITOL FORMULATION)

| Storage Temp. (°C) | Months in Storage | Appearance Plug (cake) | Upon Reconstitution | Upon Recon. Clarity | Upon Recon. Color | Residual Moisture (% by weight) | pH Upon Reconstitution | Potency CPE Bioassay (IU/mg x10⁷) | Container Closure Integrity Dye Leak Test |
|---|---|---|---|---|---|---|---|---|---|
| 4 | 0 | white | clear, colorless | — | — | 0.4 | 7.3 | 3.0 | — |
| 4 | 2 | N/A | N/A | — | — | 0.5 | — | — | — |
| 4 | 3 | white | clear, colorless | — | — | 0.5 | 7.3 | 2.9 | — |
| 4 | 4 | N/A | N/A | — | — | 0.5 | — | — | — |
| 4 | 5 | N/A | N/A | — | — | — | — | — | — |
| 4 | 6 | white | clear, slightly yellow | — | — | 0.4 | 7.3 | 2.3 | — |
| 4 | 9 | white | clear, colorless | — | — | 0.6 | 7.4 | 3.0 | — |
| 4 | 12 | white | clear, colorless | — | — | 0.5 | 7.4 | 3.1 | — |
| 4 | 18 | white | clear, colorless | <III | colorless >BY₃ | 0.8 | 7.5 | 2.9 | — |
| 4 | 24 | white | clear, slightly yellow | <II | >BY₃ | 0.6 | 7.4 | 3.2 | Pass |
| 30 | 2 | N/A | N/A | — | — | 0.6 | — | — | — |
| 30 | 3 | white | clear, colorless | — | — | 0.6 | 7.3 | 3.2 | — |
| 30 | 4 | N/A | N/A | — | — | 0.6 | — | — | — |
| 30 | 5 | N/A | N/A | — | — | — | — | — | — |
| 30 | 6 | white | clear, slightly yellow | — | — | 0.5 | 7.4 | 2.4 | — |
| 30 | 9 | white | clear, colorless | — | — | 0.7 | 7.5 | 3.2 | — |
| 30 | 12 | white | clear, colorless | — | — | 0.7 | 7.4 | 3.1 | — |
| 30 | 18 | white | clear, colorless | III | colorless >BY₃ | 1.0 | 7.4 | 3.1 | — |
| 30 | 24 | white | clear, slightly yellow | <III | — | 1.0 | — | 3.3 | Pass |
| European Specification | | White | Clear, colorless to light yellow | NMT RefIII | Colorless to slightly yellow NMT BY₃ | NMT 3% | 7.1-7.8 | 2.2 to 4.5 x10⁷ | Pass |

FIGURE 16(A)

STABILITY OF BETASERON / BETAFERON FINAL CONTAINER PRODUCT
RESULTS FOR LOT MBDPN019 (MANNITOL FORMULATION)

| Storage Temp. (°C) | Months in Storage | RP-HPLC Analysis | |
|---|---|---|---|
| | | Interferon beta-1b (Peak B + Peak B1) (mg/ml) | Peak B1 (glycosylated) (mg/ml) |
| 4 | 0 | — | — |
| 4 | 2 | — | — |
| 4 | 3 | — | — |
| 4 | 4 | 0.24 | <0.02 |
| 4 | 5 | 0.25*** | <0.02*** |
| 4 | 6 | 0.24*** | <0.02*** |
| 4 | 9 | | |
| 4 | 12 | 0.23 | <0.02 |
| 4 | 18 | 0.25 | <0.02 |
| 4 | 24 | 0.25 | <0.02 |
| 30 | 2 | — | — |
| 30 | 3 | — | — |
| 30 | 4 | 0.22 | <0.02 |
| 30 | 5 | 0.25*** | <0.02*** |
| 30 | 6 | 0.24*** | <0.02*** |
| 30 | 9 | | |
| 30 | 12 | 0.23 | <0.02 |
| 30 | 18 | 0.24 | <0.02 |
| 30 | 24 | 0.24 | <0.02 |
| Expected Results: | | 0.25 ± 0.04 | NMT 0.02 |

*** SOP QG162 (AKA QI052) was not followed: NLT one injection per test vial (two test vials per lot) was not performed
Note: A correction was made to the 18 month data point for RP-HPLC.

FIGURE 16(B)

REDUCING ACTIVITY IN MANNITOL SAMPLES

| Sample No. | Sample | Reducing Activity Content (ppm) | Mean Value (ppm) |
|---|---|---|---|
| 1 | Sample # 1 Unpurified | 53.7 | |
| 2 | Sample # 2 Unpurified | 44.1 | 44.1 |
| 3 | Sample # 3 Unpurified | 34.4 | |
| 4 | Sample # 1 Methanol Treated | 19.3 | |
| 5 | Sample # 2 Methanol Treated | 19.2 | 18.5 |
| 6 | Sample # 3 Methanol Treated | 17.0 | |
| 7 | Highly Purified Mannitol # 1 | 10.5 | |
| 8 | Highly Purified Mannitol # 2 | 11.2 | 10.2 |
| 9 | Highly Purified Mannitol # 3 | 8.9 | |

STABILIZED INTERFERON COMPOSITIONS

CROSS-REFERENCE TO RELATED APPLICATIONS

This application claims the benefit of U.S. Provisional Application Ser. No. 60/246,456, filed Nov. 7, 2000, and U.S. Provisional Application Ser. No. 60/252,224, filed Nov. 21, 2000, each of which is hereby incorporated in its entirety by reference herein.

FIELD OF THE INVENTION

The invention relates generally to pharmaceutical compositions, more particularly to stabilized liquid or lyophilized formulations of proteins, including interferon-β and others.

BACKGROUND OF THE INVENTION

The interferons are a family of glycoproteins whose secretion from cells is induced by a number of signals including viruses, double-stranded RNAs, other polynucleotides, antigens, and mitogens. Interferons exhibit multiple biological activities, including antiviral, antiproliferative, and immunomodulatory activities. At least three distinct types of human interferons, α, β, and γ, have been distinguished based on a number of factors, including anti-viral and anti-proliferative activities.

Interferon-β, (IFN-β) is the first identified effective treatment for those with multiple sclerosis (MS), and has been demonstrated to reduce the number of attacks suffered by patients with relapsing and remitting MS. IFN-β compositions are also useful in the treatment of hepatitis B and C infections.

As with all protein-based pharmaceuticals, one major obstacle that must be overcome in the use of IFN β as a therapeutic agent is the loss of pharmaceutical utility that can result from its instability in pharmaceutical formulations. Physical instabilities that threaten polypeptide activity and efficacy in pharmaceutical formulations include denaturation and formation of soluble and insoluble aggregates, while chemical instabilities include hydrolysis, imide formation, oxidation, racemization, and deamidation. Some of these changes are known to lead to the loss or reduction of the pharmaceutical activity of the protein of interest. In other cases, the precise effects of these changes are unknown, but the resulting degradative products are still considered to be pharmaceutically unacceptable due to the potential for undesirable side effects.

The instability of polypeptides in pharmaceutical preparations directly impacts their pharmaceutical utility, as the guidelines set for approval of protein-based pharmaceuticals emphasize that changes in the activity and the molecular characteristics of the polypeptide should be minimal. See, for example, the Nov. 30, 1995 report on stability testing of Biotechnological/Biological products issued by the International Conference on Harmonization of Technical Requirements for Registration of Pharmaceuticals for Human Use (a tripartite organization which makes pharmaceutical-related policy recommendations for implementation in the European Union, Japan, and the USA), which states "[w]herever significant qualitative or quantitative changes indicative of degradation product formation are detected during long-term, accelerated, and/or stress stability studies, consideration should be given to potential hazards and to the need for characterization and quantification of degradation products within the long-term stability program."

Consequently, there is a need for additional protein pharmaceutical compositions, including IFN-β compositions, comprising physiologically compatible stabilizers that are substantially free of reducing impurities, thereby stabilizing the protein and enhancing their pharmaceutical utility.

SUMMARY OF THE INVENTION

Compositions comprising IFN-β as a therapeutically active component and highly purified mannitol as an excipient are provided. The compositions are characterized by improved stability during storage in comparison with IFN-β compositions containing mannitol that is not highly purified. Methods of making these compositions are also provided.

BRIEF DESCRIPTION OF THE DRAWINGS

FIG. 12 shows the stability evaluation data for the IFN-β dextrose formulations as described in Example 2.

FIG. 13 shows the stability evaluation data for the IFN-β formulation comprising highly purified mannitol as described in Example 2.

FIG. 14 shows the stability evaluation data for Lot 006 of the IFN-β formulations comprising highly purified mannitol as described in Example 3.

FIG. 15 shows the stability evaluation data for Lot 008 of the IFN-β formulations comprising highly purified mannitol as described in Example 3.

FIG. 16 shows the stability evaluation data for Lot 009 of the IFN-β formulations comprising highly purified mannitol as described in Example 3.

FIG. 17 shows the reducing activity present in various samples of mannitol. Samples 1–3 are USP mannitol that has not been methanol extracted, carbon filtered, or ultrafiltered; samples 4–6 are USP mannitol that has been methanol extracted, and samples 7–9 are mannitol that has been methanol extracted, carbon treated, ultrafiltered, and recrystallized.

DETAILED DESCRIPTION OF THE INVENTION

Figure 1:
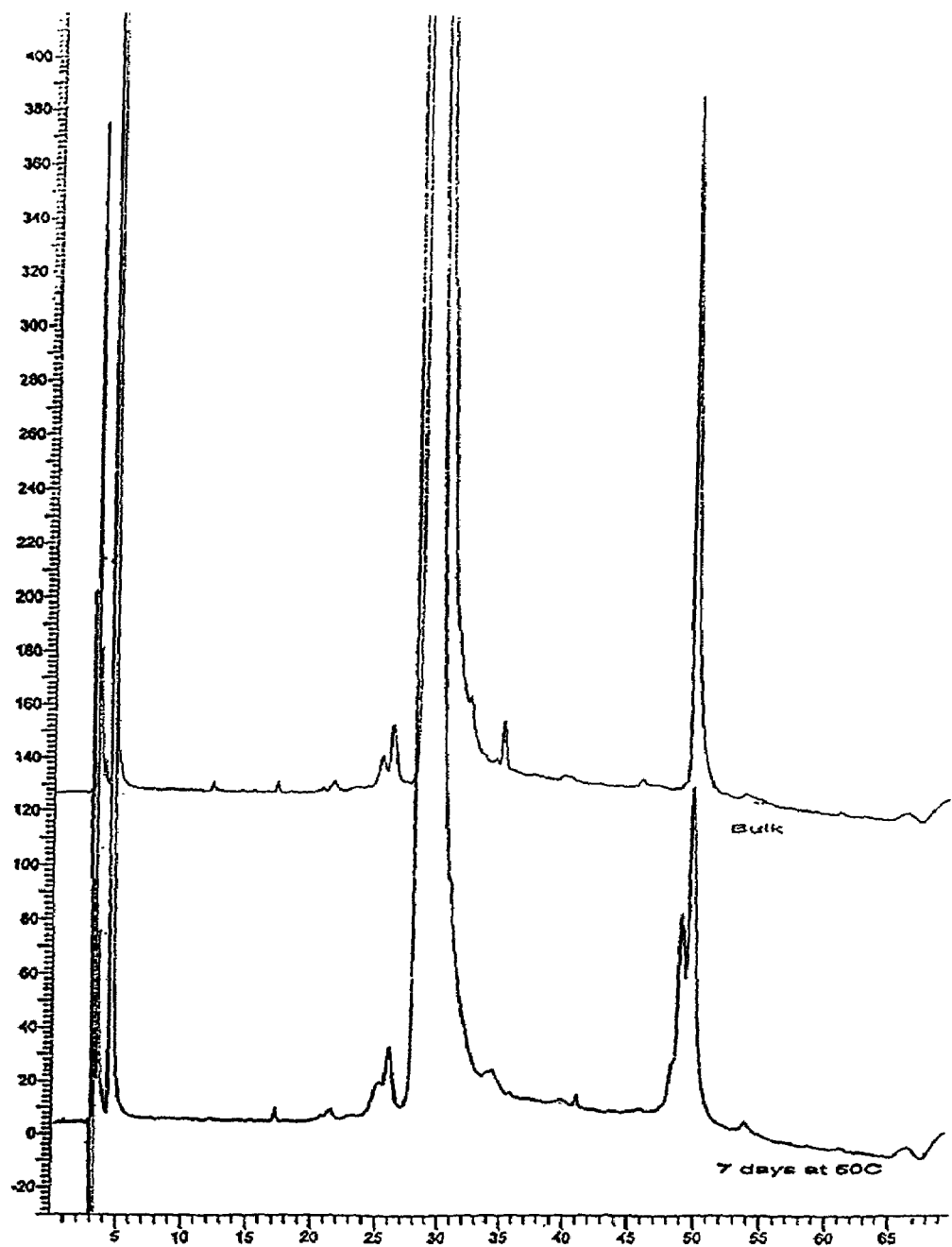
FIG. 1 shows a comparison of the RP-HPLC chromatograms for dextrose-formulated IFN-β bulk and lyophilized powder incubated at 50° C. for one week. The formation of glucosylated INF-β adducts in the formulation held at 50° C. is seen as the appearance of a second (B1) peak (at approximately fraction 48) preceding the main IFN-β peak (at approximately fractions 49–50). See Example 1.

The present invention is directed to IFN-β pharmaceutical compositions with increased stability and methods for their preparation. The compositions comprise IFN-β and highly purified mannitol. The highly purified mannitol increases the stability of the formulation by decreasing the formation of degradative products. The stabilized IFN-β formulation is advantageous in that it is safer (due to the reduction in potential harmful side-effects) and more economical (due to an increase in the shelf-life of the formulation).

The increased stability of the disclosed compositions results from the use of mannitol that has been highly purified. It is the novel finding of the present invention that mannitol that has not been highly purified contains a reducing activity that interacts with IFN-β to produce undesirable adducts (degradative products), whereas mannitol that has been highly purified does not contain this reducing activity and does not cause formation of these adducts in IFN-β formulations. Experimental results presented herein (see Example 1 in the Experimental Section) indicate that the reducing activity present in unpurified mannitol that is responsible for IFN-β adduct formation is not a reducing sugar activity because the adducts formed in the presence of mannitol that is not highly purified can be clearly differentiated from adducts formed in the presence of excipients with known reducing sugar activity (for example, dextrose).

"Highly purified mannitol" as used herein refers to mannitol having a low level of reducing activity. The reducing activity of the highly purified mannitol is less than 20 parts per million USP as measured by the reducing activity assay described elsewhere herein. In various embodiments, the reducing activity of the highly purified mannitol is less than 19 parts per million, less than 18 parts per million, less than 17 parts per million, less than 16 parts per million, less than 15 parts per million, less than 14 parts per million, or less than 13 parts per million. In one embodiment, the highly purified mannitol is USP (United States Pharmacopeia) or ACS (American Chemical Society) grade mannitol that has undergone the additional steps of:1) methanol extraction; 2) carbon treatment; 3) ultrafiltration; and 4) recrystallization. The highly purified mannitol is present at a concentration sufficient to stabilize the formulation. Formulations encompassed by the invention may have as little as about 0.1% highly purified mannitol or as much as about 7.5% highly purified mannitol (weight/volume). In various embodiments, the mannitol is present at a concentration of about 0.2% to about 7.0%, about 0.25% to about 2.5%, and about 1.25%.

Both liquid and lyophilized pharmaceutical compositions comprising IFN-β as a therapeutically active component and highly purified mannitol as an excipient are disclosed. For purposes of the present invention, the term "liquid" with regard to pharmaceutical compositions or formulations is intended to include the term "aqueous". The term "lyophilize" with regard to IFN-β pharmaceutical formulations is intended to refer to rapid freeze drying under reduced pressure of a plurality of vials, each containing a unit dose of the interferon formulation of the present invention therein. Lyophilizers, which perform the above described lyophilization, are commercially available and readily operable by those skilled in the art. In one embodiment of the present invention, the liquid composition is lyophilized.

Figure 9:
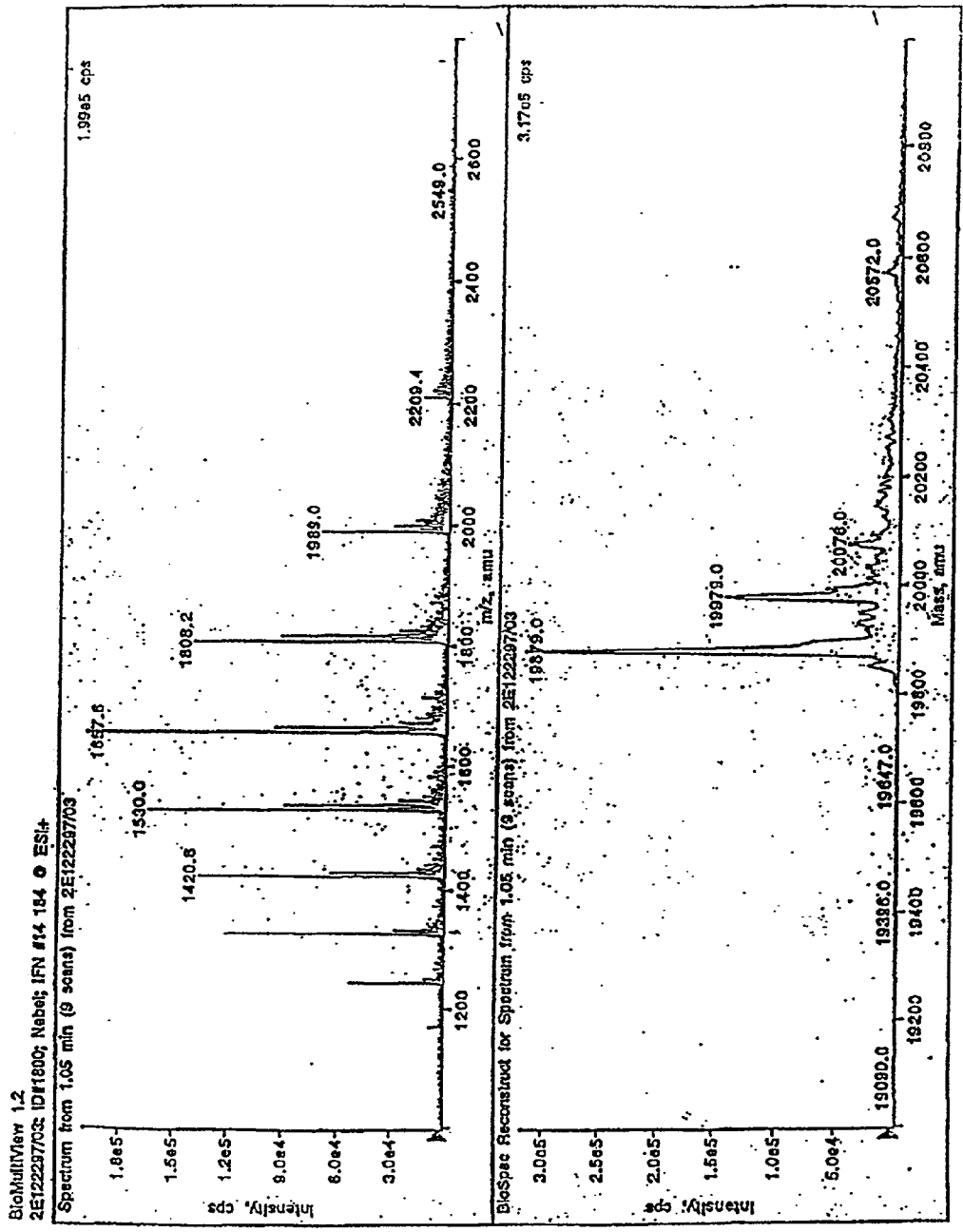
FIG. 9 shows the mass spectrum of an IFN-β formulation comprising highly purified mannitol (methanol extracted, carbon treated, ultrafiltered, and recrystallized). Only three small peaks, in addition to the predominant peak representing unmodified INF-β are seen. See Example 1.

The liquid or lyophilized IFN-β formulations of the present invention are "stabilized". By "stabilized" compositions or by compositions having "increased stability" or "improved stability", it is intended compositions that have increased storage stability relative to IFN-β compositions formulated with mannitol that has not been highly purified. This increase in stability is manifested by a decrease in the formation of IFN-β adducts or degradative products during storage in comparison to formulations with mannitol that has not been highly purified. The formation of adducts or degradative products can be measured using the mass spectrometric assay described herein. A stabilized highly purified mannitol-formulated IFN-β composition of the invention is characterized by the absence of the additional peaks that are observed in USP mannitol-formulated IFN-β when compared with an IFN-β composition formulated without mannitol, as determined by the mass spectrometric assay described herein. See, for example, the mass spectrum of IFN-β formulated with highly purified mannitol shown in FIG. 9, which shows no additional peaks in comparison with the mass spectrum of IFN-β formulated without mannitol shown in FIG. 10. In contrast, the mass spectrum of IFN-β formulated with USP mannitol shown in FIG. 11 resolves numerous additional peaks (adducts) in comparison with the mass spectrum of IFN-β formulated without mannitol. The stabilized IFN-β pharmaceutical formulations of the invention retain their potency and contain less than 0.02 mg/ml of glucosylated IFN-β for a period of up to about two years when stored at 30° C. and at least two years when stored at 25° C.

The stabilized pharmaceutical formulations of the invention comprise IFN-β and variants thereof. The term "IFN-β" as used herein refers to IFN-β or variants thereof, sometimes referred to as IFN-β-like polypeptides. Human IFN-β variants, which may be naturally occurring (e.g., allelic variants that occur at the IFN-β locus) or recombinantly produced, have amino acid sequences that are the same as, similar to, or substantially similar to the mature native IFN-β sequence. Fragments of IFN-β or truncated forms of IFN-β that retain their activity are also encompassed. These biologically active fragments or truncated forms of IFN-β are generated by removing amino acid residues from the full-length IFN-β amino acid sequence using recombinant DNA techniques well known in the art. IFN-β polypeptides may be glycosylated or unglycosylated, as it has been reported in the literature that both the glycosylated and unglycosyated IFN-β's show qualitatively similar specific activities and that, therefore, the glycosyl moieties are not involved in and do not contribute to the biological activity of IFN-β.

The IFN-β variants encompassed herein include muteins of the mature native IFN-β sequence shown in SEQ ID NO:1(see, for example, U.S. Pat. No. 5,814,485, herein incorporated by reference), wherein one or more cysteine residues that are not essential to biological activity have been deliberately deleted or replaced with other amino acids to eliminate sites for either intermolecular crosslinking or incorrect intramolecular disulfide bond formation. IFN-β, variants of this type include those containing a glycine, valine, alanine, leucine, isoleucine, tyrosine, phenylalanine, histidine, tryptophan, serine, threonine, or methionine substituted for the cysteine found at amino acid 17 of the mature native amino acid sequence. Serine and threonine are the more preferred replacements because of their chemical analogy to cysteine. Serine substitutions are most preferred. See, for example, the IFN-β variant where the cysteine found at amino acid 17 of the mature native sequence is replaced with serine (SEQ ID NO:2 U.S. Pat. No. 5,814, 485). Cysteine 17 may also be deleted using methods known in the art (see, for example, U.S. Pat. No. 4,588,584, herein incorporated by reference), resulting in a mature IFN-β mutein that is one amino acid shorter than the mature native IFN-β. See also, as examples, U.S. Pat. Nos. 4,530,787; 4,572,798; and 4,588,585. Thus, IFN-β variants with one or more mutations that improve, for example, their pharmaceutical utility are also encompassed by the present invention.

The skilled artisan will appreciate that additional changes can be introduced by mutation into the nucleotide sequences encoding IFN-β, thereby leading to changes in the IFN-β amino acid sequence, without altering the biological activity of the interferon. Thus, an isolated nucleic acid molecule encoding an IFN-β variant having a sequence that differs from the amino acid sequence for the mature native IFN-β can be created by introducing one or more nucleotide substitutions, additions, or deletions into the corresponding nucleotide sequence disclosed herein, such that one or more amino acid substitutions, additions or deletions are introduced into the encoded IFN-β. Mutations can be introduced by standard techniques, such as site-directed mutagenesis and PCR-mediated mutagenesis. Such IFN-β variants are also encompassed by the present invention.

For example, conservative amino acid substitutions may be made at one or more predicted, preferably nonessential amino acid residues. A "nonessential" amino acid residue is a residue that can be altered from the wild-type sequence of IFN-β without altering its biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Such substitutions would not be made for conserved amino acid residues, or for amino acid residues residing within a conserved motif.

Alternatively, variant IFN-β nucleotide sequences can be made by introducing mutations randomly along all or part of an IFN-β coding sequence, such as by saturation mutagenesis, and the resultant mutants can be screened for IFN-β biological activity to identify mutants that retain activity. Following mutagenesis, the encoded protein can be expressed recombinantly, and the activity of the protein can be determined using standard assay techniques described herein.

Biologically active variants of IFN-β will generally have at least 80%, more preferably about 90% to about 95% or more, and most preferably about 96% to about 99% or more amino acid sequence identity to the reference IFN-β polypeptide that serves as the basis for comparison, for example native human IFN-β. By "sequence identity" is intended the same amino acid residues are found within the variant polypeptide and the polypeptide molecule that serves as a reference when a specified, contiguous segment of the amino acid sequence of the variant is aligned and compared to the amino acid sequence of the reference molecule.

For purposes of optimal alignment of the two sequences for the purposes of sequence identity determination, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least 20 contiguous amino acid residues. Corrections for increased sequence identity associated with inclusion of gaps in the variant's amino acid sequence can be made by assigning gap penalties. Methods of sequence alignment are well known in the art.

Thus, the determination of percent identity between any two sequences can be accomplished using a mathematical algorithm. One preferred, non-limiting example of a mathematical algorithm utilized for the comparison of sequences is the algorithm of Myers and Miller (1988) *Comput. Appl. Biosci.* 4:11–7. Such an algorithm is utilized in the ALIGN program (version 2.0), which is part of the GCG alignment software package. A PAM120 weight residue table, a gap length penalty of 12, and a gap penalty of 4 can be used with the ALIGN program when comparing amino acid sequences. Another preferred, non-limiting example of a mathematical algorithm for use in comparing two sequences is the algorithm of Karlin and Altschul (1990) *Proc. Natl. Acad. Sci. USA* 90:5873–5877, modified as in Karlin and Altshcul (1993) *Proc. Natl. Acad. Sci USA* 90:5873–5877. Such an algorithm is incorporated into the NBLAST and XBLAST programs of Altschul et al. (1990) *J. Mol. Biol.* 215:403–410. BLAST amino acid sequence searches can be performed with the XBLAST program, score=50, wordlength=3, to obtain amino acid sequence similar to the polypeptide of interest. To obtain gapped alignments for comparison purposes, gapped BLAST can be utilized as described in Altschul et al. (1997) *Nucleic Acids Res.* 25:3389–3402. Alternatively, PSI-BLAST can be used to perform an interated search that detects distant relationships between molecules. See Altschul et al. (1997) supra. When utilizing BLAST, gapped BLAST, or PSI-BLAST programs, the default parameters can be used. See www.ncbi.nlm.nih.gov. Also see the ALIGN program (Dayhoff (1978) in *Atlas of Protein Sequence and Structure* 5:Suppl. 3, National Biomedical Research Foundation, Washington, D.C.) and programs in the Wisconsin Sequence Analysis Package, Version 8 (available from Genetics Computer Group, Madison, Wis.), for example, the GAP program, where default parameters of the programs are utilized.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) *Comput. Appl. Biosci.* 4:11–17.

Biologically active IFN-β variants encompassed by the invention also include IFN-β polypeptides that have covalently linked with, for example, polyethylene glycol (PEG) or albumin. These covalent hybrid IFN-β molecules possess certain desirable pharmaceutical properties such as an extended serum half-life after administration to a patient. Methods for creating PEG-IFN adducts involve chemical modification of monomethoxypolyethylene glycol to create an activated compound which will react with IFN-β. Methods for making and using PEG-linked polypeptides are described, for example in Delgado et al. (1992) *Crit. Rev. Ther. Drug. Carrier Syst.* 9:249–304. Methods for creating albumin fusion polypeptides involve fusion of the coding sequences for the polypeptide of interest (e.g., IFN-β) and albumin and are described in U.S. Pat. No. 5,876,969, herein incorporated by reference. These hybrid IFN-β molecules will react with the impurities present in USP mannitol and will be more stable when formulated with highly purified mannitol.

Biologically active variants of IFN-β encompassed by the invention should retain IFN-β activities, particularly the ability to bind to IFN-β receptors. In some embodiments, the IFN-β variant retains at least about 25%, about 50%, about 75%, about 85%, about 90%, about 95%, about 98%, about 99% or more of the biologically activity of the reference IFN-β polypeptide, for example native human IFN-β. IFN-β variants whose activity is increased in comparison with the activity of the reference IFN-β polypeptide are also encompassed. The biological activity of IFN-β variants can be measured by any method known in the art. Examples of such assays can be found in Fellous et al. (1982) *Proc. Natl. Acad. Sci USA* 79:3082–3086; Czerniecki et al. (1984) *J. Virol.* 49(2):490–496; Mark et al. (1984) *Proc. Natl Acad. Sci. USA* 81:5662–5666; Branca et al. (1981) *Nature* 277:221–223; Williams et al. (1979) *Nature* 282:582–586; Herberman et al. (1979) *Nature* 277:221–223; Anderson et al. (1982) *J. Biol. Chem.* 257(19):11301–11304; and the IFN-β potency assay described herein (see Example 2).

The IFN-β of the formulations of the invention can be from any animal species including, but not limited to, avian, canine, bovine, porcine, equine, and human. Preferably, the IFN-β is from a mammalian species when the formulation is to be used in treatment of a mammalian IFN-β disorder, and more preferably is from a mammal of the same species as the mammal undergoing treatment for such a disorder.

Non-limiting examples of IFN-β polypeptides and IFN-β variant polypeptides encompassed by the invention are set forth in Nagata et al. (1980) *Nature* 284:316–320; Goeddel et al. (1980) *Nature* 287:411–416; Yelverton et al. (1981) *Nucleic Acids Res.* 9:731–741; Streuli et al. (1981) *Proc. Natl. Acad. Sci. U.S.A.* 78:2848–2852; EP028033B1, and EP109748B1. See also U.S. Pat. Nos. 4,518,584; 4,569,908; 4,588,585; 4,738,844; 4,753,795; 4,769,233; 4,793,995; 4,914,033; 4,959,314; 5,545,723; and 5,814,485. These disclosures are herein incorporated by reference. These citations also provide guidance regarding residues and regions of the IFN-β polypeptide that can be altered without the loss of biological activity.

In one embodiment of the present invention, the IFN-β within the stabilized pharmaceutical formulations is the mature native IFN-β polypeptide. In another embodiment, the IFN-β in these formulations is the mature IFN-β polypeptide wherein the cysteine found at amino acid 17 of the mature native sequence is replaced with serine as discussed above. However, the present invention encompasses other embodiments where the IFN-β within the stabilized pharmaceutical formulation is any biologically active IFN-β polypeptide or variant as described elsewhere herein.

In some embodiments of the present invention, the IFN-β is recombinantly produced. By "recombinantly produced IFN-β " is intended IFN-β that has comparable biological activity to mature native IFN-β and that has been prepared by recombinant DNA techniques. IFN-β can be produced by culturing a host cell transformed with an expression vector comprising a nucleotide sequence that encodes an IFN-β polypeptide. The host cell is one that can transcribe the nucleotide sequence and produce the desired protein, and can be prokaryotic (for example, *E. coli*) or eukaryotic (for example a yeast, insect, or mammalian cell). Examples of recombinant production of IFN-β are given in Mantei et al. (1982) *Nature* 297:128; Ohno et al (1982) *Nucleic Acids Res.* 10:967; Smith et al, (1983) *Mol. Cell. Biol.* 3:2156, and U.S. Pat. Nos. 4,462,940, 5,702,699, and 5,814,485; herein incorporated by reference. See also U.S. Pat. No. 5,795,779, where IFN-β1a is recombinantly produced in Chinese hamster ovary (CHO) cells; herein incorporated by reference. Human interferon genes have been cloned using recombinant DNA ("rDNA") technology and have been expressed in *E. coli* (Nagola et al. (1980) *Nature* 284:316; Goeddel et al. (1980) *Nature* 287:411; Yelverton et al. (1981) *Nuc. Acid Res.* 9:731; Streuli et al. (1981) *Proc. Natl. Acad. Sci. U.S.A.* 78:2848). Alternatively, IFN-β can be produced by a transgenic animal or plant that has been genetically engineered to express the IFN-β protein of interest in accordance with methods known in the art.

Alternatively, IFN-β can be synthesized chemically, by any of several techniques that are known to those skilled in the peptide art. See, for example, Li et al (1983) *Proc. Natl. Acad. Sci. USA* 80:2216–2220, Steward and Young (1984) *Solid Phase Peptide Synthesis* (Pierce Chemical Company, Rockford, Ill.), and Baraney and Merrifield (1980) *The Peptides: Analysis, Synthesis, Biology*, ed. Gross and Meinhofer, Vol. 2 (Academic Press, New York, 1980), pp. 3–254, discussing solid-phase peptide synthesis techniques; and Bodansky (1984) *Principles of Peptide Synthesis* (Springer-Verlag, Berlin) and Gross and Meinhofer, eds. (1980) *The Peptides: Analysis, Synthesis, Biology*, Vol. 1 (Academic Press, New York), discussing classical solution synthesis. IFN-β can also be chemically prepared by the method of simultaneous multiple peptide synthesis. See, for example, Houghten (1984) *Proc. Natl. Acad. Sci. USA* 82:5131-5135; and U.S. Pat. No. 4,631,211.

Compositions encompassed by the invention may have as little as about 0.01 mg/ml IFN-β and as much as about 15 mg/ml IFN-β (weight/volume). In various embodiments, the IFN-β is present at a concentration of about 0.015 mg/ml to about 12.5 mg/ml, about 0.025 mg/ml to about 10 mg/ml, about 0.05 mg/ml to about 8 mg/ml, about 0.075 mg/ml to about 6 mg/ml, about 0.1 mg/ml to about 4 mg/ml, about 0.125 mg/ml to about 2 mg/ml, about 0.175 mg/ml to about 1 mg/ml, about 0.2 mg/ml to about 0.5 mg/ml, about 0.225 mg/ml to about 0.3 mg/ml, and about 0.25 mg/ml.

In some embodiments, the formulations of the invention comprise a pharmaceutically acceptable carrier. By "pharmaceutically acceptable carrier" is intended a carrier that is conventionally used in the art to facilitate the storage, administration, and/or the healing effect of the therapeutic ingredients. A carrier may also reduce any undesirable side effects of the IFN-β. A suitable carrier should be stable, i.e., incapable of reacting with other ingredients in the formulation. It should not produce significant local or systemic adverse effects in recipients at the dosages and concentrations employed for treatment. Such carriers are generally known in the art. Suitable carriers for this invention are those conventionally used large stable macromolecules such as albumin, gelatin, collagen, polysaccharide, monosaccharides, polyvinyl-pyrrolidone, polylactic acid, polyglycolic acid, polymeric amino acids, fixed oils, ethyl oleate, liposomes, glucose, sucrose, lactose, mannose, dextrose, dextran, cellulose, sorbitol, polyethylene glycol (PEG), and the like. Slow-release carriers, such as hyaluronic acid, may also be suitable. See particularly Prisell et al. (1992) *Int. J. Pharmaceu.* 85:51–56, and U.S. Pat. No. 5,166,331. Other acceptable components in the composition include, but are not limited to, pharmaceutically acceptable agents that modify isotonicity including water, salts, sugars, polyols, amino acids, and buffers. Examples of suitable buffers include phosphate, citrate, succinate, acetate, and other organic acids or their salts and salts that modify the tonicity such as sodium chloride, sodium phosphate, sodium sulfate, potassium chloride, and can also include the buffers listed above.

In some embodiments of the present invention, the pharmaceutically acceptable carrier is human albumin. The human albumin may be naturally-occurring human albumin or recombinantly produced human albumin; these two forms are referred to collectively herein as "human albumin". Formulations encompassed by the invention may have as little as about 0.01% human albumin and as much as about 15% human albumin (weight/volume). In various embodiments, the human albumin is present at a concentration of about 0.025% to about 12.5%, about 0.05% to about 10%, about 0.1% to about 9%, about 0.25% to about 8%, about 0.5% to about 7%, about 0.6% to about 2%, about 0.7% to about 1.75%, about 0.75% to about 1.5%, about 1.2% to about 1.3%, and about 1.25%.

The pharmaceutical composition may additionally comprise a solubilizing agent or solubility enhancer. Compounds containing a guanidinium group, most preferably arginine, are suitable solubility enhancer for IFN-β. Examples of such solubility enhancers include the amino acid arginine, as well as amino acid analogues of arginine that retain the ability to enhance solubility of IFN-β. Such analogues include, without limitation, dipeptides and tripeptides that contain arginine. Additional suitable solubilizing agents are discussed in U.S. Pat. Nos. 4,816,440; 4,894,330; 5,004,605; 5,183,746; 5,643,566; and in Wang et al. (1980) *J. Parenteral Drug Assoc.* 34:452–462; herein incorporated by reference.

Non-limiting examples of solubilizing agents encompassed by the present invention include surfactants (detergents) that have a suitable hydrophobic-hydrophilic balance to solubilize IFN-β. Strong natural or synthetic anionic surfactants such as alkali metal salts of fatty acids and alkali metal alkyl sulfates may be used. Such agents will usually contain 10 to 14 carbon atoms. Sodium dodecyl sulfate (SDS) and sodium laurate are particularly preferred solubilizing agents. Examples of other solubilizing agents that can be used in compositions of the invention include but are not limited to sodium dodecyl sulfonate, sodium decyl sulfate, sodium tetradecyl sulfate, sodium tridecyl sulfonate, sodium myristate, sodium caproylate, sodium dodecyl N-sarcosinate, and sodium tetradecyl N-sarcosinate. Classic stabilization of pharmaceuticals by surfactants or emulsifiers is described, for example, in Levine et al. (1991) *J. Parenteral Sci. Technol.* 45(3):160–165. Additional suitable surfactants are discussed in U.S. Pat. Nos. 4,507,281; 4,816,440; and 5,183,746; herein incorporated by reference.

In addition to those agents disclosed above, other stabilizing agents, such as ethylenediaminetetracetic acid (EDTA) or one of its salts such as disodium EDTA, can be added to further enhance the stability of the liquid pharmaceutical compositions. The EDTA acts as a scavenger of metal ions known to catalyze many oxidation reactions, thus providing an additional stabilizing agent.

Where the IFN-β formulation is used for delivery to a mammal such as a human, the isotonicity of the composition is also a consideration. Thus, in one embodiment, the composition for an injectable solution of IFN-β will provide an isotonicity the same as, or similar to, that of patient serum or body fluids. To achieve isotonicity, a salt, such as sodium chloride, potassium, chloride, or a phosphate buffer, can be added to the solution at an appropriate concentration.

The pH of the formulation is also a consideration. The stabilized IFN-β formulations of the invention have a pH ranging from about 3.0 to about 9.0. Suitable pH ranges include, for example, about 4.0 to about 8.8, about 5.0 to about 8.6, about 6.0 to about 8.4, about 6.8 to about 8.2, about 6.9 to about 8.0, about 7.0 to about 7.8, about 7.1 to about 7.7, about 7.2 to about 7.6, and about 7.3 to about 7.5.

A pharmaceutically effective amount of a stabilized liquid IFN-β formulation, or of a reconstituted stabilized lyophilized IFN-β pharmaceutical formulation of the invention is administered to a subject. By "pharmaceutically effective amount" is intended an amount that is useful in the treatment, prevention, or diagnosis of a disease or condition. Typical routes of administration include, but are not limited to, oral administration, nasal delivery, pulmonary delivery, and parenteral administration, including transdermal, intravenous, intramuscular, subcutaneous, intraarterial, and intraperitoneal injection or infusion. In one such embodiment, the administration is by injection, preferably subcutaneous injection. Injectable forms of the compositions of the invention include, but are not limited to, solutions, suspensions, and emulsions. Typically, a therapeutically effective amount of IFN-β comprises about 0.01 μg/kg to about 5 mg/kg of the composition, preferably about 0.05 μg/kg to about 1000 μg/kg, more preferably about 0.1 μg/kg to about 500 μg/kg, even more preferably still about 0.5 μg/kg to about 30 μg/kg.

In one embodiment, the stabilized pharmaceutical composition comprising IFN-β is formulated in a unit dosage and may be in an injectable or infusible form such as solution, suspension, or emulsion. Furthermore, it can be stored frozen or prepared in the dried form, such as lyophilized powder, which can be reconstituted into the liquid solution, suspension, or emulsion before administration by any of various methods including oral or parenteral routes of administration. The stabilized pharmaceutical composition may be sterilized by membrane filtration and is stored in unit-dose or multi-dose containers such as sealed vials or ampules. Additional methods for formulating a pharmaceutical composition generally known in the art may be used to further enhance storage stability of the pharmaceutical compositions disclosed herein provided they do not adversely affect the beneficial effects of the highly purified mannitol as disclosed. A thorough discussion of formulation and selection of pharmaceutically acceptable carriers, stabilizers, etc. can be found in *Remington's Pharmaceutical Sciences* (1990) (18th ed., Mack Pub. Co., Eaton, Pa.), herein incorporated by reference.

In some embodiments, the liquid compositions of the invention are packaged in a syringe (the "pre-filled" syringe of the invention). In one embodiment, the pre-filled syringe comprising a composition of the invention may then be frozen. This frozen pre-filled syringe is useful for storage or transportation purposes.

The following examples are offered by way of illustration and not by way of limitation.

EXPERIMENTAL

Example 1

Development of an IFN-β Pharmaceutical Formulation with Increased Stability I. Introduction IFN-β pharmaceutical formulations containing dextrose as an excipient are known in the art. When such formulations are incubated at a temperature of 37° C. or above, the dextrose in these formulations forms covalent adducts with the IFN-β that can be detected by RP-HPLC (reverse-phase high performance liquid chromatography). IFN-β formulated with USP mannitol does not form RP-HPLC-detectable covalent adducts under the same conditions. However, USP mannitol contains impurities that combine with IFN-β to form adduct species detected by electrospray mass spectrometry. The nature of the impurities in USP mannitol is unknown. The formation of these adducts (or degradative products) is considered to be pharmaceutically undesirable and even pharmaceutically unacceptable, as current guidelines for polypeptide-based pharmaceuticals emphasize the importance of minimizing the formation of degradative products in formulations. Degradative products are considered to be undesirable or unacceptable because they increase the chance that the polypeptide-based pharmaceutical will cause unwanted side effects. It is the novel finding of the present invention that IFN-β shows increased stability when it is formulated with mannitol that is highly purified such that its reducing activity is less than 20 parts per million in comparison with when it is formulated with mannitol that is not highly purified. It is the further novel finding of the present invention that purification of USP mannitol by extraction with methanol, carbon treatment, ultrafiltration, and recrystallization results in a mannitol preparation with a reducing activity of less than 20 parts per million.

II. Methods

IFN-β-1b for use in these experiments was produced in *E. coli* essentially as described in U.S. Pat. Nos. 4,462,940 and 5,702,699; herein incorporated by reference. Sodium dodecyl sulfate and salts were removed from the IFN-β by chromatography; and the IFN-β-1b was combined with a solution of human albumin at a pH of 11.5–12.0; the pH of the solution was adjusted to 7.5 with HCl; and a solution containing the excipient (mannitol or dextrose) was added to bring the final concentration to 1.25%. The final concentration of human albumin in the formulation was 1.25% w/v.

IFN-β-1b from these formulations was prepared for mass spectrometry by RP HPLC. This method allows quantitation of glucosylated IFN-β-1b after it is resolved as a separate peak (B1) on the chromatogram. The limit of detection for glucosylated IFN-β-1b with this method is 0.02 mg/ml. When the amount of this peak is less than 0.02 mg/ml, the two peak areas are summed and compared to an unformulated IFN-β reference to obtain total IFN-β-1b content. When the peak area is greater than 0.02 mg/ml, its concentration is determined independently and reported.

The following equipment and their respective manufacturers' instruction manuals were used for analysis.
 Solvent Delivery System: Waters 626 Gradient Pump
 Injection System: Waters 717 plus Autosampler
 200 ml injection loop
 polypropylene autosampler vials with Teflon septa
 refrigerated autosampler temperature control set to 4° C.
 84% acetonitrile is used as the needle wash.
 Column heater: Waters 600
 Set column heater to 40° C.
 Column: BAKERBOND Wide-Pore Butyl C4 RP-Column, 300 Å 5 μm, 4.6 mm (ID) 250 mm, J. T. Baker part number 22010.

The column is connected in the direction of solvent flow, as indicated on the column label, and placed in a column heater.
 Detector: Waters 486 UV Detector.
 Wavelength is set to 214 nm.
 Data system input is unattenuated.
 Data System: P.E. Nelson Turbochrom Data System Lyophilized IFN-β formulation samples were reconstituted with 1.20 ml of 0.54% sodium chloride, gently inverted to mix, and incubated at ambient temperature for 30±5 minutes. The calibrator is an unformulated IFN-β reference. The calibrator stock solution is diluted to approximately 0.5 mg/ml, and the concentration of the diluted calibrator solution is determined by UV absorbance (mean of 6 replicates). The final concentration of the diluted calibrator solution is the mean of UV absorbance readings divided by 1.7 (the IFN-β-1b extinction coefficient). The diluted calibrator solution concentration is determined by absorbance to 3 significant figures. The calibrator solution was then diluted to 0.25 mg/ml for use as a working calibrator solution.

The autosampler was programmed to inject 20 μl per injection at 70 minute intervals. The data system voltage range was 1 volt, the sampling rate was 1 point per second, and the acquisition time was 70 minutes. Eluent A was 0.1% TFA (Trifluoroacetic acid, HPLC grade), and Eluent B was 84% acetonitrile (HPLC grade) and 0.084% TFA (HPLC grade). The eluent flow rate was set to 1.0 ml/minute (70% Eluent A and 30% Eluent B), and the column was equilibrated for one hour. After the detector baseline and system were equilibrated, a gradient blank was analyzed. Analysis began when no significant peaks were present in the second gradient blank.

IFN-β concentration is determined from the sum of the area of the peaks corresponding to unmodified IFN-β (the "B" peak) and glucosylated IFN-β (the "B1" peak). For example, where the calibrator solution is unformulated IFN-β at 0.25 mg/ml, the IFN-β concentration (mg/ml)=(test sample total peak area B 1+B/calibrator total peak area B1+B)×0.25 mg/ml.

The electrospray mass spectra (ES-MS) data were obtained using fractions from this chromatography. Fractions of each peak were collected and concentrated before the analysis. Electrospray mass spectra were obtained using an API 100 single-quadruple mass spectrometer (Perkin-Elmer Sciex Instruments, Thornhill, Ontario, Canada) interfaced to a Harvard syringe pump (Harvard Apparatus, South Natick, Mass.) and a Rheodyne 8125 injector with 100 μM i.d. fused silca tubing. Mass spectra were recorded in the positive mode by scanning a mass/charge ratio (m/z) range of 140 to 2500 at 6 s/scan using a step size of 0.2 Da. The mass spectrometer was calibrated using a polypropylene glycol mixture containing $3.3 \times 10^{-5}$ M PPG 425, $1 \times 10^{-4}$ M PPG 1000 and $2 \times 10^{-4}$ PPG 2000 (Aldrich Chemical Co.) in 50:50:0.1 water:methanol:formic acid (v:v:v) containing 2 mM ammonium acetate. An aliquot of the protein solution (20–50 pM in 2 μL) was introduced into the mass spectrometer ion source in 49:40:1 water:acetonitrile:acetic acid at 20 μL/mm. Since proteins are introduced into the ion source at low pH, the basic sites (e.g., nitrogen atoms in the side chains of arginine, lysine, and histidine residues) are protonated to varying degrees resulting in molecular ions with multiple charge states, e.g. $[M+H]^+$, $[M+2H]^{2+}$, depending on the number of sites accessible for protonation. The detector records the m/z ratios of the molecular ions in the various charge states and the mass spectra can be deconvoluted using Biotoolbox software (Perkin-Elmer Sciex Instruments) to obtain the protein molecular mass. The mass accuracy of molecular mass measurement at 20 kDa was within 2 kDa.

The reducing activity of the mannitol was determined by a modification of the USP protocol. The protocol measures the reduction of $Cu^{2+}$ in alkaline solution in the presence of bicinchoninic acid (BCA, Pierce, prepared according to the manufacturers instructions). The BCA complexes with $Cu^{1+}$, and this complex has a blue color with a peak absorbance (A) at 562 nm.

Two mannitol samples (500 μl of a 150 mg/ml mannitol solution) were assayed for each condition. The standard curve was generated using serial dilutions of a glucose solution with known reducing activity. 500 μl of the prepared BCA solution was added to each test sample, standard sample, and blank and incubated at 60° C. for 40 minutes. The glucose standards were fit to a linear curve, and the reducing activity of the mannitol test samples (in ppm) was calculated as (($A_{562}$ of mannitol sample/slope of standard curve)/(mannitol content in mg/ml) (1000))$\times 10^6$.

III. Results and Discussion

Figure 2:
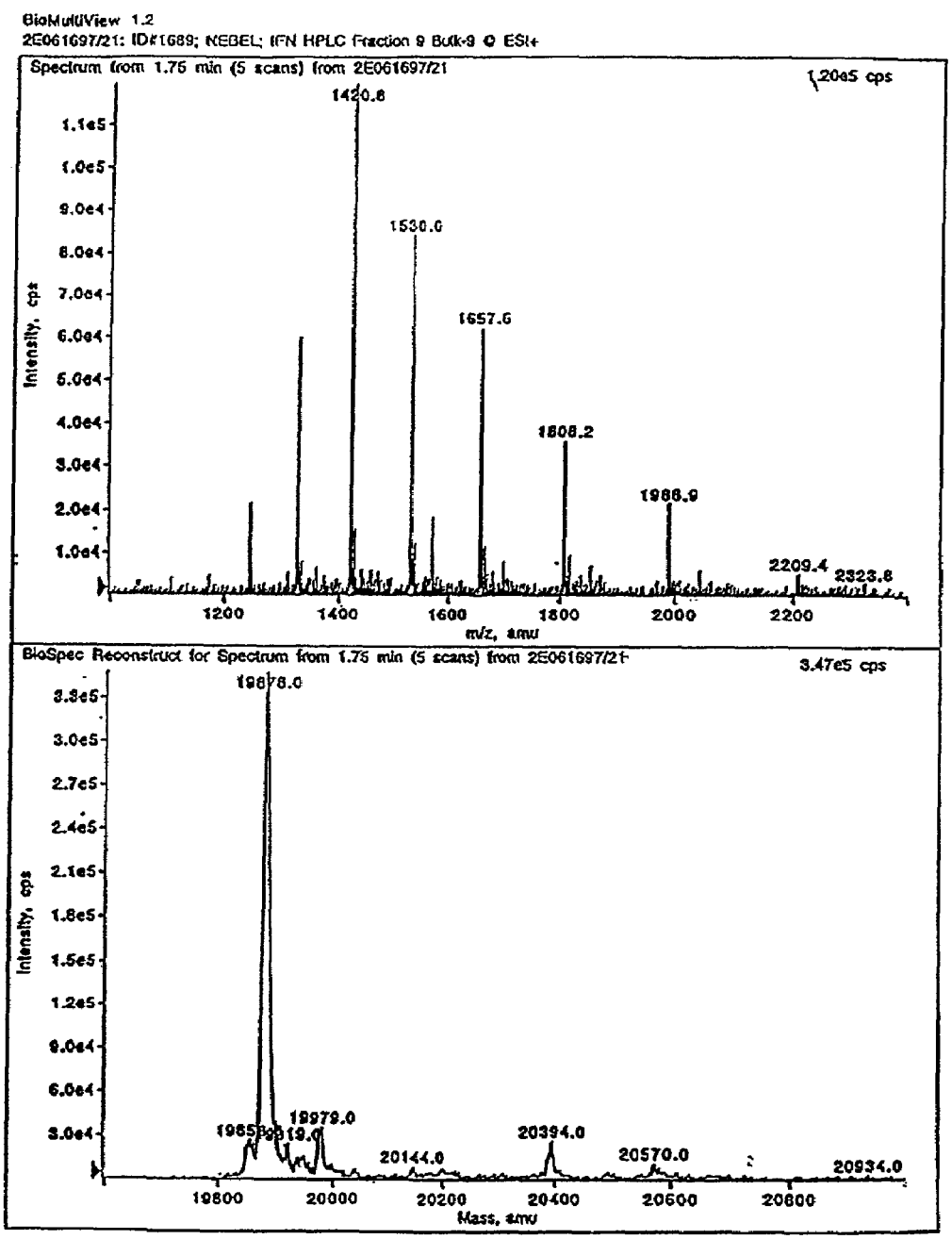
FIG. 2 shows the mass spectrum for bulk dextrose-formulated IFN-β. Several small peaks are detectable in addition to the main IFN-β peak at 19878 amu. See Example 1.
Figure 3:
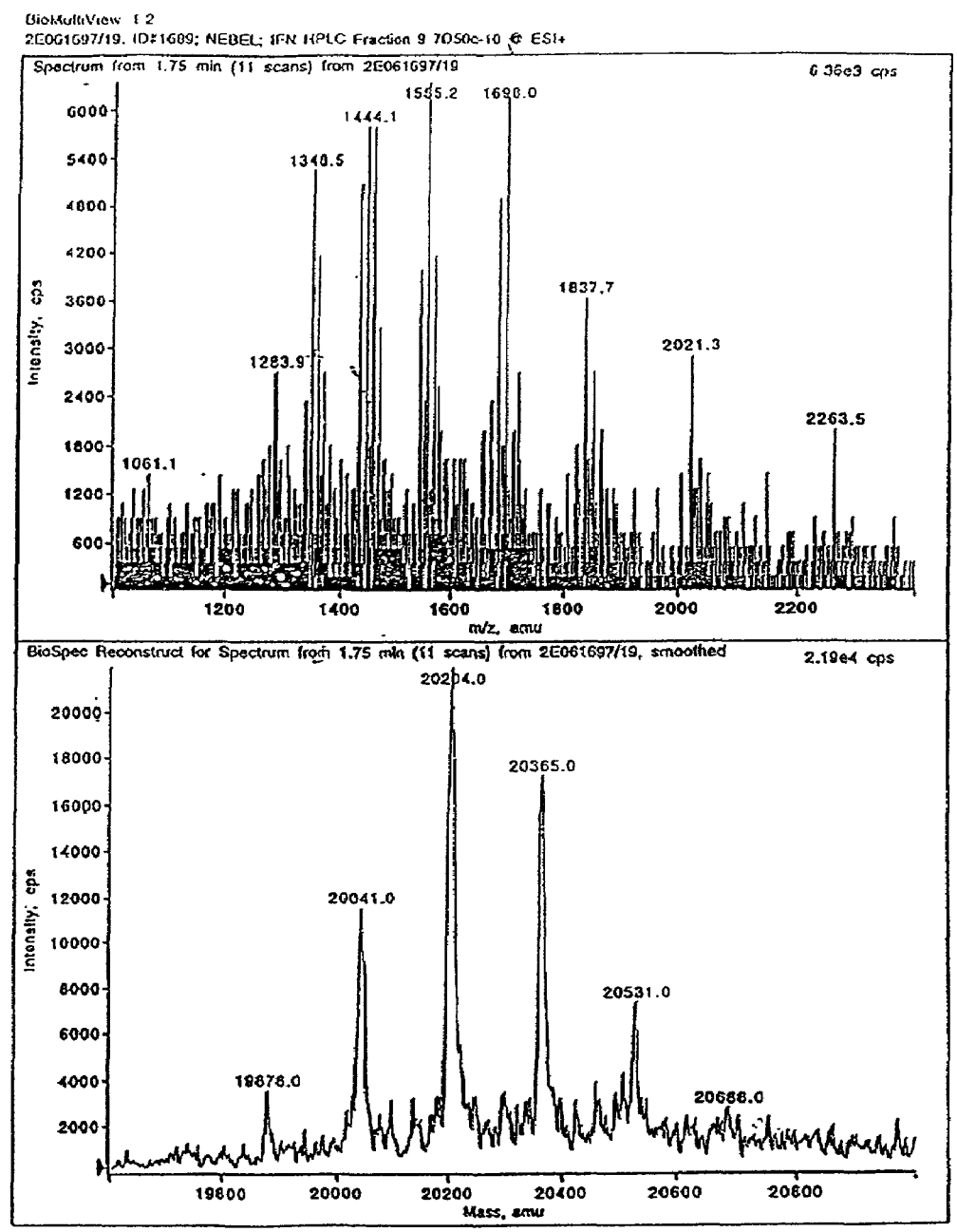
FIG. 3 shows the mass spectrum for a sample of dextrose-formulated IFN-β lyophilized from the bulk composition and stored at 50° C. for 1 week. In contrast to FIG. 2, the predominant peaks correspond to IFN-β adducts. See Example 1.

Glucosylation was detected in the dextrose formulation using mass spectrometry as multiples of 162 Daltons added to the molecular mass of IFN-β-1b. Analysis of IFN-β-1b peptides has suggested that these adducts result from reaction of reducing sugars with protein lysine residues (Amadori reactions). FIG. 1 compares the RP-HPLC chromatogram of the formulated bulk of the dextrose formulation to the freeze dried formulation stored at 50° C. for 1 week. The figure shows that the IFN-β-1b in the dextrose formulation reacts readily at 50° C. to produce the B1 peak in the freeze-dried state. The ES-MS of the formulated bulk (FIG. 2) has no peaks associated with glucose adducts (plus 162). In contrast, the mass spectra of the incubated freeze-dried dextrose formulation (FIG. 3) shows extensive modification. Thus, the glucose reacts with the IFN-β-1b to form species that are detected by RP-HPLC whose structure is confirmed by ES-MS.

Figure 4:
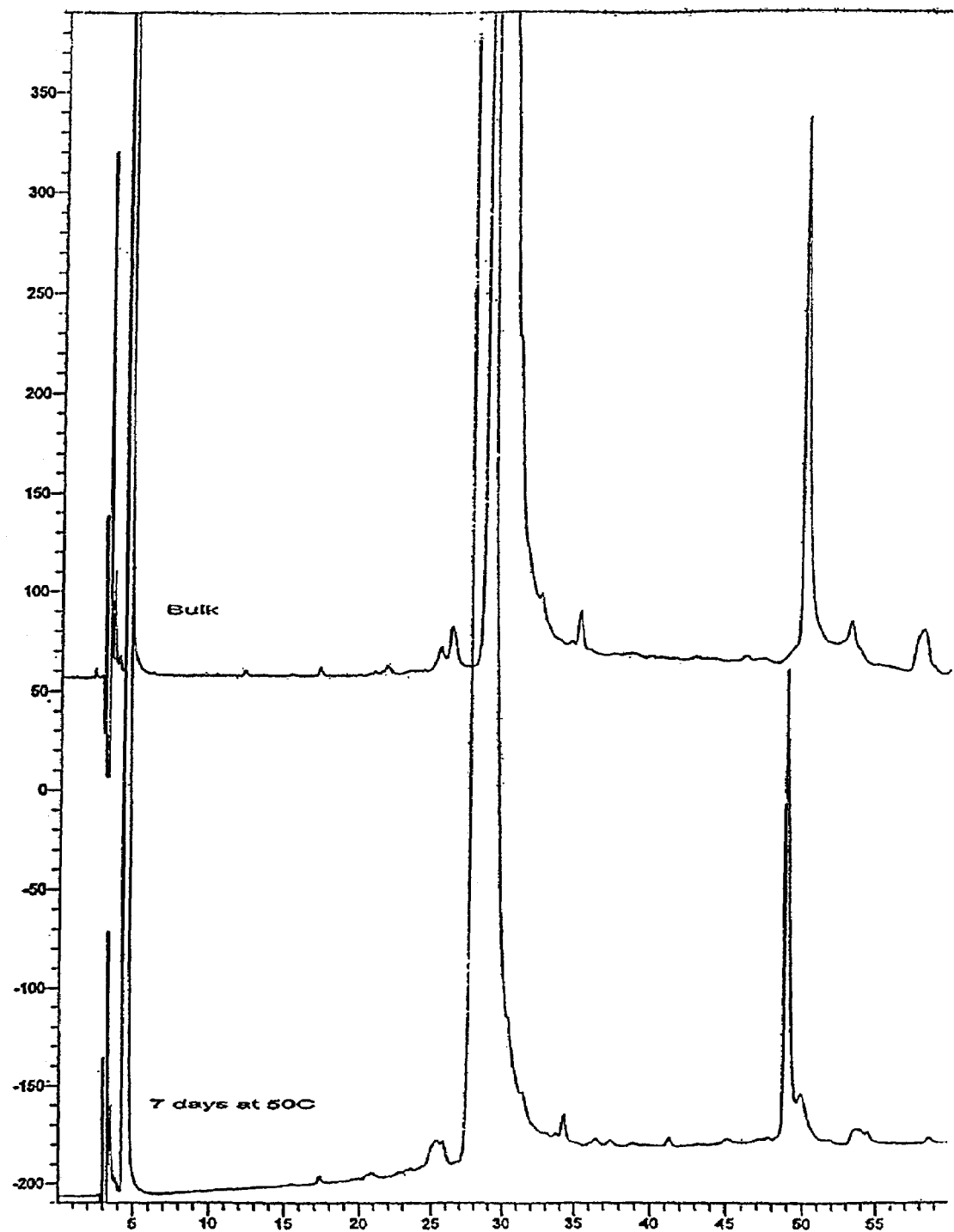
FIG. 4 shows a comparison of the RP-HPLC chromatograms for USP mannitol-formulated IFN-β bulk and lyophilized powder incubated at 50° C. for one week. The formation of glucosylated IFN-β adducts in the formulation held at 50° C. (appearance of the B1 peak) is not seen. See Example 1.
Figure 5:
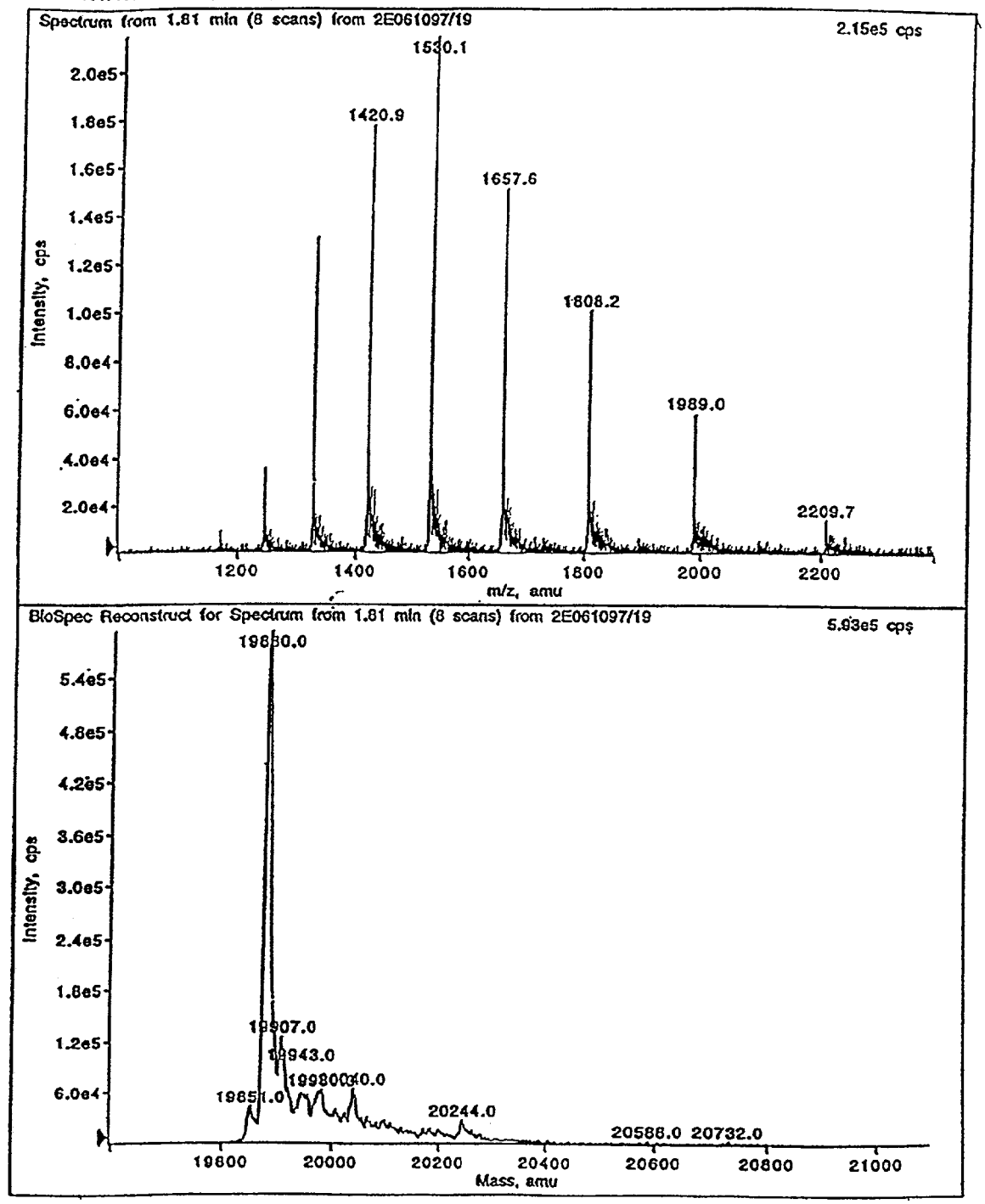
FIG. 5 shows the mass spectrum of USP mannitol-formulated IFN-β bulk. IFN-β, is detected as a peak at 19880 amu. See Example 1.
Figure 6:
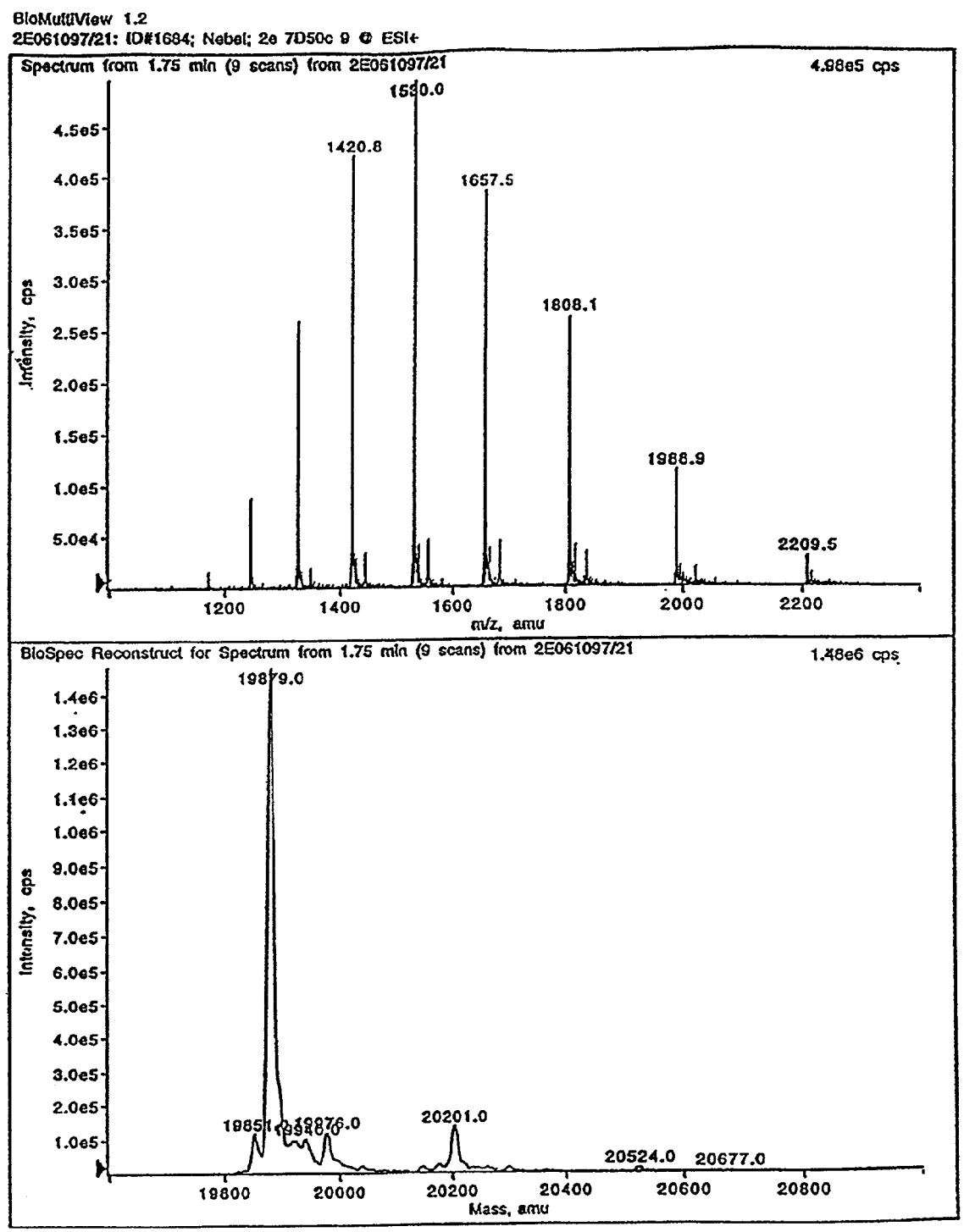
FIG. 6 shows the mass spectrum of USP mannitol-formulated IFN-β that has been lyophilized and incubated at 50° C. for 1 week. The formation of additional peaks (representing adducts) can be seen in the spectrum. See Example 1.

In contrast, an IFN-β-1b formulation made with USP mannitol does not form species that are detectable as peak B1 by RP-HPLC. FIG. 4 compares the mannitol formulated bulk to the freeze-dried formulation held for 7 days at 50° C. Clearly, no peak B1 is formed. However, the mass spectra of the formulated bulk in FIG. 5 shows the presence of a peak at 20040, and the mass spectrum of the incubated freeze-dried mannitol formulation in FIG. 6 has a new peak at 20201. The amount of adducts formed with mannitol can not be quantitated by ES-MS; however, the signals for the adducts are often near the limit of detection for the instrument. The mechanism of the formation of these peaks is not known. The reaction of the mannitol with IFN-β-1b does not form species like the species formed with dextrose or glucose; no peak B1is formed. Thus, the data indicate that a purer form of mannitol is needed to prevent the formation of IFN-β-1b adducts.

Figure 7:
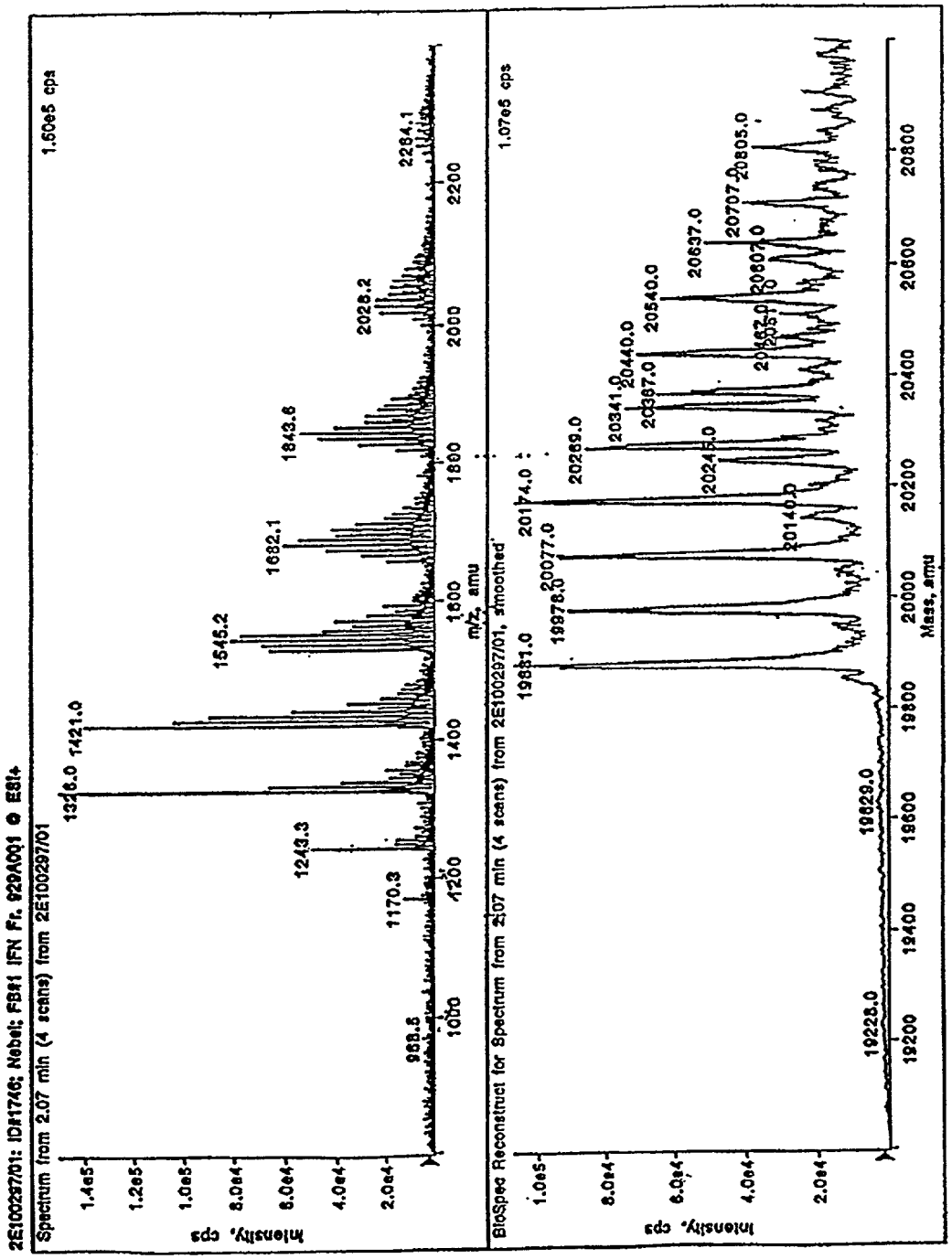
FIG. 7 shows the mass spectrum of unpurified mannitol-formulated IFN-β. The formation of numerous additional peaks (representing adducts) can be seen in this spectrum. See Example 1.
Figure 8:
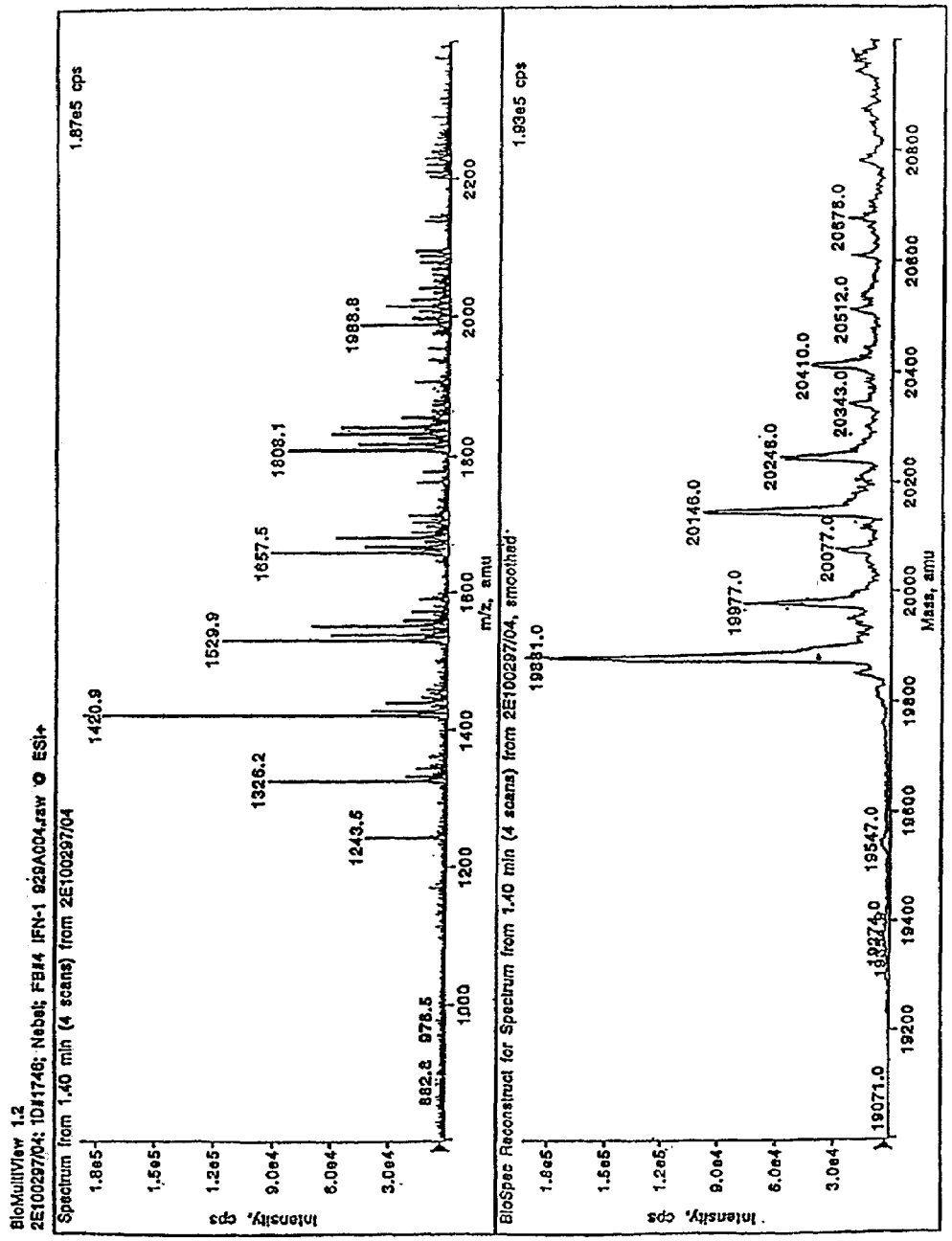
FIG. 8 shows the mass spectrum of IFN-β formulated with methanol-extracted mannitol from the same lot used in FIG. 7. The size and number of the adduct peaks has been substantially reduced. See Example 1.

Mannitol that had been methanol extracted to reduce impurities was then tested for its effects on the stability of IFN-β-1b. IFN-β-1b was formulated with three different lots of methanol-extracted mannitol, and the formulated bulk and final container test samples were assayed using the RP-HPLC and ES-MS assays described above. FIG. 7 shows the mass spectrum of IFN-β-1b formulated with untreated mannitol, and FIG. 8 shows the mass spectrum of the IFN-β-1b formulated with the same lot of mannitol that was purified with methanol. All three lots of mannitol showed a similar pattern. FIG. 17 shows that methanol treatment removes greater than half of the reducing activity. Clearly, the methanol treatment removes impurities that form complexes with IFN-β-1b, but some may not be fully removed by this treatment.

Figure 10:
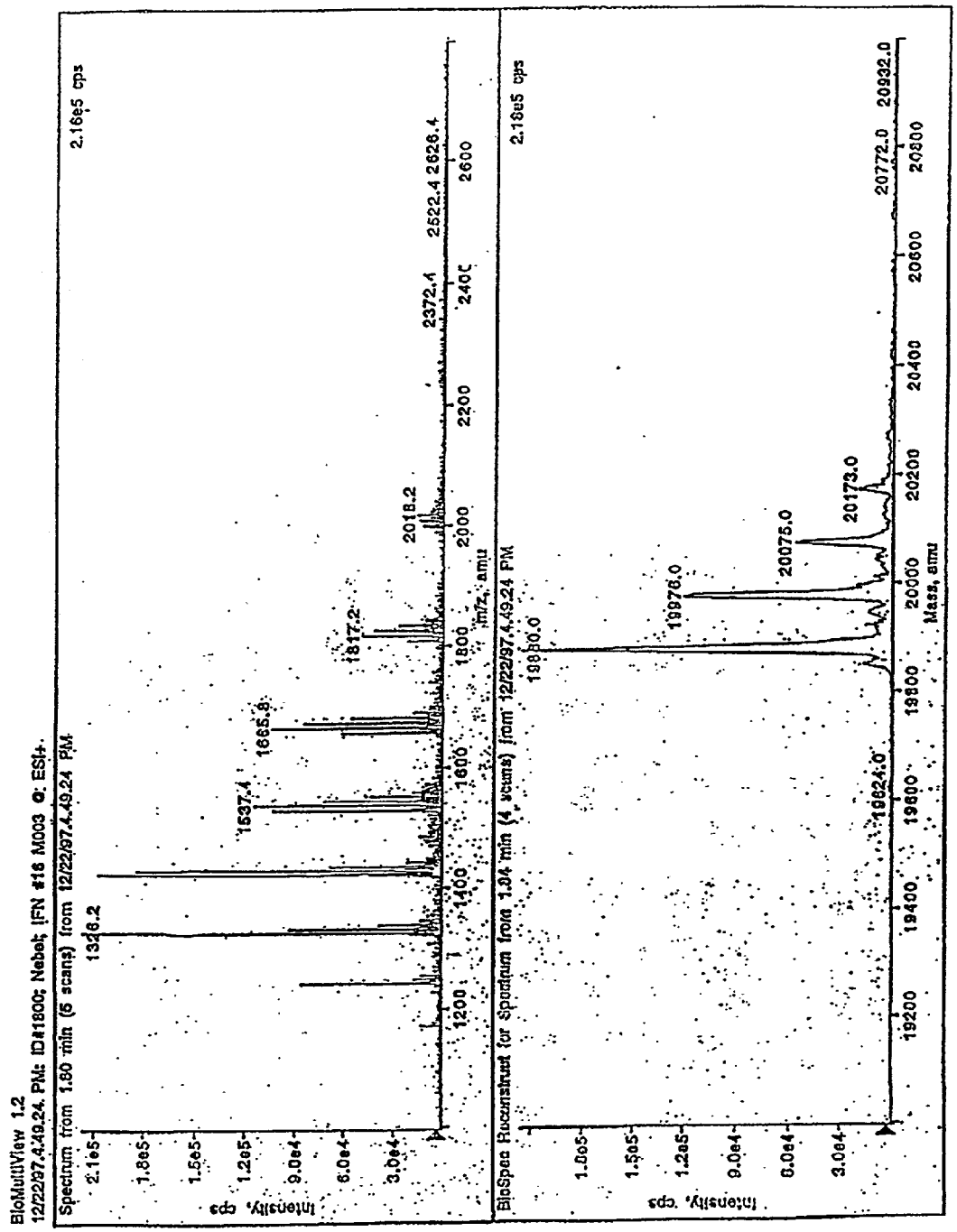
FIG. 10 shows the mass spectrum of IFN-β formulated in the absence of mannitol. From this spectrum, it can be seen that the predominant secondary peaks present in FIG. 9 are not formed by interaction with highly purified mannitol, as they appear in the absence of excipient as well. See Example 1.
Figure 11:
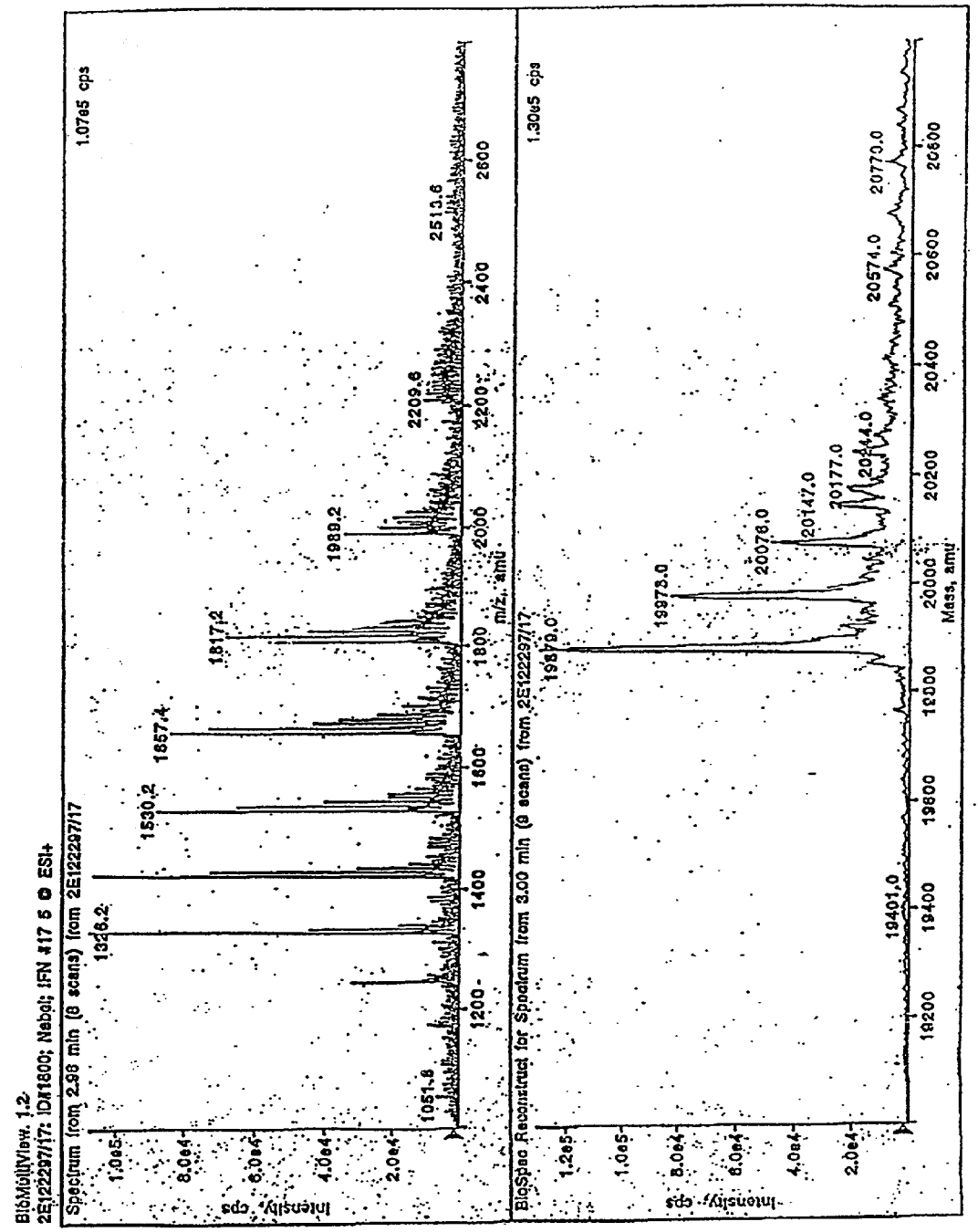
FIG. 11 shows the mass spectrum of IFN-β formulated with USP mannitol, run on the same day as FIG. 9 above. This spectrum confirms that IFN-β formulated with USP mannitol forms additional peaks (adducts) that are not present in an IFN-β formulation comprising highly purified mannitol. See Example 1.

To reduce the remaining impurities in the mannitol, three additional steps were added to the purification process. These additional steps are carbon treatment, ultrafiltration, and recrystallization. Three lots of methanol-extracted, carbon-treated, ultrafiltered, and recrystallized mannitol were tested as above. The colorimetric reducing activity assay demonstrated that the additional purification steps lowered the reducing activity content to about 10 ppm (see FIG. 17, samples 7–9). A formulation was prepared with the highly purified mannitol. A mass spectrum of the formulation prepared with the highly purified mannitol (FIG. 9) revealed no additional peaks that were not present in formulated bulk prepared without mannitol and run on the same day as a negative control (FIG. 10). A mass spectrum of a formulation prepared with USP mannitol (FIG. 11) was also run the same day as a positive control. Thus the additional treatment of the mannitol yields a product that is low in reducing activity and does not appear to react with IFN-β-1b by ES-MS.

Example 2

Stability of IFN-β Formulations Comprising Highly Purified Mannitol: Short-Term Accelerated Study I. Introduction Experimental formulations of IFN-β-1b were prepared with dextrose and mannitol, as described above, and an accelerated stability study was performed to compare these formulations. The stability of the formulation was tested under two different conditions. The first was to subject the formulations to high temperature stress, and the second was to measure stability upon long-term storage at room temperature. No changes were detected in the formulation comprising highly purified mannitol after storage at 25° C. for 3 months, and the potency of the formulation remained essentially unchanged after storage at 37° C. for 3 months or at 50° C. for 1 month.

II. Methods

Samples of each formulation were stored at 8° C., 25° C., or 37° C. for 3 months. In addition, at the two month time point, samples were taken from each temperature and stored at 50° C. for an additional month. The purpose of the 50° C. shift was to exacerbate potential changes that may have taken place in the first two months of storage and thus allow a better determination of whether placement at 25° C. and 37° C. for 2 months predisposes the product to a more rapid degradation when returned to the original storage temperature of 8° C.

The specific activity of the IFN-β-1b was assayed as follows. A549 human lung carcinoma cells (ATCC CCL 185) and murine encephalomyocarditis virus, strain EMC (ATCC VR-129B) were obtained from American Type Culture Collection. Formulation samples were reconstituted with 1.2 mls diluent (0.54% NaCl), serially diluted in Growth/Assay Media, and added to a 96-well assay plate along with IFN-β-1b standards. The volume of diluted IFN-β in each well was 100 μl. A549 cells in Growth/Assay Medium (Eagle's MEM with Earle's salts and 2.2 g/L sodium bicarbonate, 8.9% Fetal Bovine Serum, 1.79 mM L-glutamine, 89U/ml penicillin, and 89 μg streptomycin/ml) were added at a concentration of $1 \times 10^4$ cells/well. The plate was then incubated in a humidified 37°±2° C., 5±1% $CO_2$ incubator. At the end of this incubation, cells were infected with EMC virus at a multiplicity of infection of between 5 and 16. The plates were then incubated for 24±1 hour in a humidified 37°±2° C., 5±1% $CO_2$ incubator. The cells were stained with pre-warmed (37° C.) MTT (3-[4,5 Dimethylthiazol-2-yl]-2,5-diphenyltetrazolium bromide, 5 mg/ml, 50 μl/well), and incubated as before for 3.5 to 4.5 hours. The medium was aspirated from the cells, and 100 μl stain solubilizing solution (81% v/v 2-propanol, 3 % w/v sodium dodecyl sulfate, 0.04 N HCl) was added to each well. Plates were then incubated for 30–60 minutes at ambient temperature in the dark. Plates were then shaken for 8±3 minutes on a microplate shaker. Finally, the absorbance of each well at 570 nm was measured on a microplate spectrophotometer. The activity of IFN-β activity standards was fit to a linear regression curve, and the activities of the test samples were determined from this curve. The specific activity of each sample was calculated based on the mass of sample used.

RP-HPLC analysis of IFN-β-1b concentration was performed as described above. Adduct formation was also monitored in reduced SDS-PAGE Western blots as an apparent increase in the molecular weight of the IFN-β-1b band.

III. Results and Discussion

The potency (specific activity) of the mannitol formulations remained essentially unchanged during the study, while that of the dextrose formulations increased. Exposure to temperatures of 37° C. for 1 month had no effect on the potency (See FIGS. 14 and 15). For the mannitol IFN-β1b formulation, the amount of glucosylated IFN-β-1b remained below the limit of detection for the duration of the study, even at 50° C. In contrast, glucosylation was detected in the dextrose formulation after 2 months at 37° C. and after 2 weeks at 50° C. Extensive glucosylation modified the chromatogram too much to measure the total IFN-β-1b content. Adduct formation in the dextrose formation was also detected in the reduced SDS-PAGE Western blots after 2 months storage at 37° C. or 1 month storage at 50° C., but not after 3 months storage at 25° C. In contrast, no changes in the SDS-PAGE Western blot were observed for the mannitol formulation under any of the storage conditions.

Example 3

Long-term Stability of IFN-β Formulations Comprising Highly Purified Mannitol

Three lots (N006, N008, and N009) of IFN-β-1b formulations comprising highly purified mannitol were stored at 4° C., 25° C., or 30° C. and the stability was assayed at three month intervals for one year, and at six month intervals for an additional year. Stability was assayed by the methods described above.

All three lots retained potency through twenty-four months at 4° C. and 30° C. Data are presented in FIGS. 16–18. In addition, all three lots demonstrated no more than 0.02 mgs/ml of peak B1 (glucosylated IFN-β species) at all temperatures and time points tested. Those skilled in the art will recognize, or be able to ascertain using no more than routine experimentation, many equivalents to the specific embodiments of the invention described herein for IFN-β. In addition, those skilled in the art will recognize, or be able to ascertain using no more than routing experimentation, that the above experiments and formulations provided using IFN-β as an example, are applicable to proteins in general, and most particularly pharmaceutical proteins. The pharmaceutical proteins, include, but are not limited to, the following proteins: human growth hormone, all interferons, all interleukins, colony stimulating factors (GM-CSF, G-CSF, M-CSF), beta-glucocerebrosidase, thyrotropins, etanercept, monoclonal antibodies (e.g., abciximab, basiliximab, palivizumab, rituximab, and transtuzumab) blood factors (e.g., Factor VIIa and Factor VIII), enzymes (e.g., urokinase, asparginase, anistreplase, and alteplase). Such equivalents are intended to be encompassed by the following claims.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

That which is claimed:

1. A composition comprising biologically active interferon-β (IFN-β) and highly purified mannitol wherein said biologically active IFN-β has the ability to bind to IFN-β receptors and said highly purified mannitol has a reducing activity of less than 20 parts per million.

2. The composition of claim 1, wherein said composition is characterized by increased stability.

3. The composition of claim 1, wherein said composition is lyophilized.

4. The composition of claim 1, wherein said composition is a liquid.

5. The composition of claim 1, wherein said highly purified mannitol is present at a concentration of about 0.25% to about 5% by weight per volume.

6. The composition of claim 1, wherein said IFN-β is present at a concentration of 0.01 mg/ml to 15 mg/ml.

7. The composition of claim 1, wherein said formulation has a pH within a range of about pH 3.0 to about pH 9.0.

8. The composition of claim 1, also comprising human albumin.

9. The composition of claim 8, wherein said human albumin is present at a concentration of about 0.01% to about 15% by weight per volume.

10. A composition comprising biologically active interferon-β (IFN-β) and highly purified mannitol, wherein said IFN-β is recombinant human-IFN-β and has the ability to bind to IFN-β receptors, said recombinant human IFN-β is present at a concentration of about 0.01 mg/ml to about 15 mg/ml, said highly purified mannitol has a reducing activity of less than 20 parts per million and is present at a concentration of about 0.25% to about 5% by weight per volume, the pH of the composition is about 3.0 to about 9.0, and the composition additionally comprises human albumin at a concentration of about 0.01% to about 15% by weight per volume.

11. The composition of claim 10, wherein said composition is lyophilized.

12. The composition of claim 10, wherein said composition is a liquid or is frozen.

13. The composition of claim 10, further comprising sufficient sodium chloride to render the composition isotonic.

14. The composition of claim 13, wherein said composition is lyophilized.

15. The composition of claim 13, wherein said composition is a liquid or frozen.

16. A composition comprising biologically active interferon-β (IFN-β) and highly purified mannitol, wherein the IFN-β is recombinant human-IFN-β and has the ability to bind to IFN-β receptors, said recombinant human IFN-β is present at a concentration of about 0.05 mg/ml to about 1 mg/ml, said highly purified mannitol has a reducing activity of less than 20 parts per million and is present at a concentration of about 0.25% to about 2.5% by weight per volume, the pH of the composition is about 6.8 to about 8.2, and the composition additionally comprises human albumin at a concentration of about 0.25% to about 2.5% by weight per volume.

17. The composition of claim 16, further comprising sufficient sodium chloride to render the composition isotonic.

18. The composition of claim 16, wherein said composition is a liquid, wherein said liquid is frozen or lyophilized.

19. The composition of claim 17, wherein said composition is a liquid, wherein said liquid is frozen or lyophilized.

20. A composition comprising biologically active interferon-β (IFN-β) and highly purified mannitol, wherein the IFN-β is recombinant human-IFN-β and has the ability to bind to IFN-β receptors, said recombinant human IFN-β is present at a concentration of about 0.25 mg/ml, said highly purified mannitol has a reducing activity of less than 20 parts per million and is present at a concentration of about 1.25% by weight per volume, the pH of the composition is about 7.3 to about 7.5, and the composition additionally comprises human albumin at a concentration of about 1.25% by weight per volume.

21. The composition of claim 20, further comprising sufficient sodium chloride to render the composition isotonic.

22. The composition of claim 20, wherein said composition is a liquid, wherein said liquid is frozen or lyophilized.

23. The composition of claim 21, wherein said composition is a liquid, wherein said liquid is frozen or lyophilized.

24. The composition of claim 1, wherein said biologically active IFN-β has the amino acid sequence set forth in SEQ ID NO:1 or SEQ ID NO:2.

25. The composition of claim 24, wherein said IFN-β is glycosylated or unglycosylated.

26. The composition of claim 1, wherein said IFN-β is recombinantly produced.

27. A pre-filled syringe comprising the composition of claim 1.

28. The pre-filled syringe of claim 27, wherein said composition is frozen.

29. A composition comprising a pharmaceutical polypeptide and highly-purified mannitol wherein said highly-purified mannitol has a reducing activity of less than 20 parts per million.

30. The composition of claim 29, wherein said pharmaceutical polypeptide is selected from the group consisting of human growth hormone, interferon, interleukin, granulocyte-macrophage colony stimulating factor, granulocyte colony stimulating factor, macrophage colony stimulating factor, beta-glucocerebrosidase, thyrotropins, etanercept, monoclonal antibodies, factor VIIa, factor VIII, urokinase, asparginase, anistreplase, and alteplase.

31. A method of producing a formulation of biologically active interferon-β (IFN-β) characterized by improved stability, said method comprising producing a formulation comprising said IFN-β and highly purified mannitol in an amount sufficient to stabilize said IFN-β wherein said biologically active INFβ has the ability to bind to IFN-β receptors and said highly purified mannitol has a reducing activity of less than 20 parts per million.

32. A formulation made according to the method of claim 31.

33. A method of producing a formulation of biologically active interferon-β (IFN-β) having the ability to bind to IFN-β receptors, comprising the steps of:
    a) removing sodium dodecyl sulfate and salts from the IFN-β by chromatography;
    b) combining said IFN-β with a solution of human albumin at a pH of about 11.5 to about 12.0;
    c) adjusting the pH of the solution to 7.5 with HCl; and
    d) adding a solution of highly purified mannitol having a reducing activity of less than 20 parts per million.

34. A formulation produced according to the method of claim 33.

35. The method of claim 33, further comprising the step of lyophilizing the formulation.

36. A method for increasing the stability of biologically active interferon-β (IFN-β) in a pharmaceutical composition, said method comprising incorporating into said composition highly purified mannitol in an amount sufficient to stabilize said IFN-β, wherein said IFN-β has the ability to bind to IFN-β receptors and said highly purified mannitol has a reducing activity of less than 20 parts per million.

37. The method of claim 33, further comprising the step of adding sufficient sodium chloride to render the composition isotonic.

38. A formulation produced according to the method of claim 37.

39. The method of claim 37, further comprising the step of lyophilizing the formulation.

40. The composition of claim 1, wherein said biologically active IFN-β has at least 80% amino acid sequence identity with the amino acid sequence set forth in SEQ ID NO:1 as calculated using the ALIGN program with a PAM 120 weight residue table, a gap length penalty of 12, and a gap penalty of 4.

41. The composition of claim 1, wherein said highly purified mannitol has a reducing activity of less than 15 parts per million.

42. The composition of claim 1, wherein said highly purified mannitol has a reducing activity of at least 8.9 parts per million.

43. The composition of claim 2, wherein said composition contains less than 0.02 mg/ml of glucosylated IFN-β.

44. The composition of claim 43, wherein said composition contains less than 0.02 mg/ml of glucosylated IFN-β when stored at 25° C. for a period of at least one month.

45. The composition of claim 44, wherein said composition contains less than 0.02 mg/ml of glucosylated IFN-β when stored at 25° C. for a period of at least three months.

46. The composition of claim 43, wherein said composition contains less than 0.02 mg/ml of glucosylated IFN-β when stored at 30° C. for a period of at least two months.

47. The composition of claim 46, wherein said composition contains less than 0.02 mg/ml of glucosylated IFN-β when stored at 30° C. for a period of at least six months.

48. The composition of claim 47, wherein said composition contains less than 0.02 mg/ml of glucosylated IFN-β when stored at 30° C. for a period of at least twelve months.

49. The composition of claim 48, wherein said composition contains less than 0.02 mg/ml of glucosylated IFN-β when stored at 30° C. for a period of at least two years.

50. The composition of claim 10, wherein said biologically active IFN-β has at least 80% amino acid sequence identity with the amino acid sequence set forth in SEQ ID NO:1 as calculated using the ALIGN program with a PAM 120 weight residue table, a gap length penalty of 12, and a gap penalty of 4.

51. The composition of claim 10, wherein said highly purified mannitol has a reducing activity of less than 15 parts per million.

52. The composition of claim 10, wherein said highly purified mannitol has a reducing activity of at least 8.9 parts per million.

53. The composition of claim 10, wherein said biologically active IFN-β has the amino acid sequence set forth in SEQ ID NO:1 or SEQ ID NO:2.

54. The composition of claim 13, wherein said highly purified mannitol has a reducing activity of less than 15 parts per million.

55. The composition of claim 13, wherein said highly purified mannitol has a reducing activity of at least 8.9 parts per million.

56. The composition of claim 16, wherein said recombinantly produced IFN-β has at least 80% amino acid sequence identity with the amino acid sequence set forth in SEQ ID NO:1 as calculated using the ALIGN program with a PAM 120 weight residue table, a gap length penalty of 12, and a gap penalty of 4.

57. The composition of claim 16, wherein said highly purified mannitol has a reducing activity of less than 15 parts per million.

58. The composition of claim 16, wherein said highly purified mannitol has a reducing activity of at least 8.9 parts per million.

59. The composition of claim 20, wherein said recombinantly produced IFN-β has at least 80% amino acid sequence identity with the amino acid sequence set forth in SEQ ID NO:1 as calculated using the ALIGN program with a PAM 120 weight residue table, a gap length penalty of 12, and a gap penalty of 4.

60. The composition of claim 20, wherein said highly purified mannitol has a reducing activity of less than 15 parts per million.

61. The composition of claim 20, wherein said highly purified mannitol has a reducing activity of at least 8.9 parts per million.

62. The composition of claim 29, wherein said highly purified mannitol has a reducing activity of less than 15 parts per million.

63. The composition of claim 29, wherein said highly purified mannitol has a reducing activity of at least 8.9 parts per million.

64. The method of claim 31, wherein said formulation contains less than 0.02 mg/ml of glucosylated IFN-β.

65. The method of claim 64, wherein said formulation contains less than 0.02 mg/ml of glucosylated IFN-β when stored at 25° C. for a period of at least one month.

66. The method of claim 64, wherein said formulation contains less than 0.02 mg/ml of glucosylated IFN-β when stored at 30° C. for a period of at least two months.

67. The method of claim 66, wherein said formulation contains less than 0.02 mg/ml of glucosylated IFN-β when stored at 30° C. for a period of at least six months.

68. The method of claim 31, wherein said biologically active IFN-β has at least 80% amino acid sequence identity with the amino acid sequence set forth in SEQ ID NO:1 as calculated using the ALIGN program with a PAM 120 weight residue table, a gap length penalty of 12, and a gap penalty of 4.

69. The method of claim 31, wherein said highly purified mannitol has a reducing activity of less than 15 parts per million.

70. The method of claim 31, wherein said highly purified mannitol has a reducing activity of at least 8.9 parts per million.

71. The method of claim 31, wherein said biologically active IFN-β has the amino acid sequence set forth in SEQ ID NO:1 or SEQ ID NO:2.

72. The method of claim 33, wherein said biologically active IFN-β has at least 80% amino acid sequence identity with the amino acid sequence set forth in SEQ ID NO:1 as calculated using the ALIGN program with a PAM 120 weight residue table, a gap length penalty of 12, and a gap penalty of 4.

73. The method of claim 33, wherein said highly purified mannitol has a reducing activity of less than 15 parts per million.

74. The method of claim 33, wherein said highly purified mannitol has a reducing activity of at least 8.9 parts per million.

75. The method of claim 36, wherein said biologically active IFN-β has at least 80% amino acid sequence identity with the amino acid sequence set forth in SEQ ID NO:1 as calculated using the ALIGN program with a PAM 120 weight residue table, a gap length penalty of 12, and a gap penalty of 4.

76. The method of claim 36, wherein said highly purified mannitol has a reducing activity of less than 15 parts per million.

77. The method of claim 36, wherein said highly purified mannitol has a reducing activity of at least 8.9 parts per million.

\* \* \* \* \*

SEQUENCE LISTING

<160> NUMBER OF SEQ ID NOS: 2

<210> SEQ ID NO 1
<211> LENGTH: 166
<212> TYPE: PRT
<213> ORGANISM: Homo sapiens

<400> SEQUENCE: 1

Met Ser Tyr Asn Leu Leu Gly Phe Leu Gln Arg Ser Ser Asn Phe Gln
 1               5                   10                  15

```
Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Leu Phe Arg Gln Asp Ser Ser Thr Gly Trp Asn
 65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
        130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 2
<211> LENGTH: 166
<212> TYPE: PRT
<213> ORGANISM: Artificial Sequence
<220> FEATURE:
<223> OTHER INFORMATION: C17S mutein of human IFN-beta

<400> SEQUENCE: 2

Met Ser Tyr Asn Leu Leu Gly Phe Leu Gln Arg Ser Ser Asn Phe Gln
 1               5                  10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Leu Phe Arg Gln Asp Ser Ser Ser Thr Gly Trp Asn
 65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
        130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```